(12) United States Patent
Rapoport et al.

(10) Patent No.: US 6,649,702 B1
(45) Date of Patent: Nov. 18, 2003

(54) STABILIZATION AND ACOUSTIC ACTIVATION OF POLYMERIC MICELLES FOR DRUG DELIVERY

(75) Inventors: Natalya Rapoport, Sandy, UT (US); William G. Pitt, Orem, UT (US)

(73) Assignees: University of Utah Research Foundation, Salt Lake City, UT (US); Brigham Young University, Provo, UT (US)

( * ) Notice: Subject to any disclaimer, the term of this patent is extended or adjusted under 35 U.S.C. 154(b) by 0 days.

(21) Appl. No.: 09/979,481

(22) PCT Filed: May 19, 2000

(86) PCT No.: PCT/US00/14081

§ 371 (c)(1),
(2), (4) Date: Aug. 7, 2002

(87) PCT Pub. No.: WO00/69942

PCT Pub. Date: Nov. 23, 2000

Related U.S. Application Data

(60) Provisional application No. 60/134,929, filed on May 19, 1999.

(51) Int. Cl.[7] .......................... C08L 53/00; C08L 51/00; A61K 9/00
(52) U.S. Cl. ...................... 525/299; 525/280; 525/284; 525/327.3; 523/201; 524/504; 524/505; 424/486; 424/487; 424/489
(58) Field of Search ................................. 525/299, 280, 525/284, 327.3; 523/201; 524/504, 505; 424/486, 487, 489

(56) References Cited

U.S. PATENT DOCUMENTS 6,201,065 B1 * 3/2001 Pathak et al. ................. 525/90

* cited by examiner

*Primary Examiner*—Nathan M. Nutter
*Assistant Examiner*—Olga Asinovsky
(74) *Attorney, Agent, or Firm*—TraskBritt

(57) ABSTRACT

Methods are disclosed in which a micelle is stabilized against degradation upon dilution. The micelle comprises molecules of a block polymer having a hydrophobic block and a hydrophilic block. The hydrophobic block forms a core of the micelle with corona from the hydrophilic block. The methods for stabilizing the core are (1) by chemically cross-linking, (2) incorporating a hydrophobic oil (vegetable oil) in the core to render it more hydrophobic and stable, and (3) incorporating a cross-linked interpenetrating network of a stimuli-responsive hydrogel into the core. The hydrogel is responsive to any stimuli, but preferably temperature or pH. A substance such as, drugs, can be incorporated into the dense inner core of the micelles.

When subjected to ultrasound, the micelles release the substance, and then reversibly revert to a stable dense core and re-encapsulating the substance when the ultrasound is turned off. By pulsing the ultrasound, it is therefore, to controllably release the substance in a pulsed manner corresponding to the ultrasound signal.

39 Claims, 20 Drawing Sheets

STABILIZATION AND ACOUSTIC ACTIVATION OF POLYMERIC MICELLES FOR DRUG DELIVERY

RELATED APPLICATIONS

This application claims priority from U.S. Provisional Application No. 60/134929, filed May 19, 1999, and from International Application under the Patent Cooperation Treaty PCT/US00/14081, filed May 19, 2000.

STATEMENT REGARDING FEDERALLY SPONSORED RESEARCH OR DEVELOPMENT

This work was supported by the NSF VPW grant #9550423, NIH Grant#R01 52216, and NIH grant R01 CA76562-01A1.

FIELD OF THE INVENTION

This invention relates to stabilization of micelles, and activation of micelles for delivery of substances such as drugs.

BACKGROUND OF THE INVENTION

The efficacy of cancer chemotherapy is limited by toxic side effects of anticancer drugs. The ideal scenario would be to sequester the drug in a package that would have minimal interaction with healthy cells, then at the appropriate time, release the drug from the sequestering container at the tumor site. To achieve this goal, various long-circulating colloid drug delivery systems have been designed during the last three decades. A common structural motif of all these long circulating systems, whether they be nanoparticles, liposomes, or micelles, is the presence of poly(ethylene oxide) (PEO) at their surfaces. The dynamic PEO chains prevent particle opsonization and render them "unrecognizable" by reticulo-endothelial system (RES). [1] This invaluable advantage has promoted extensive research to develop new techniques to coat particles with PEO, techniques ranging from physical adsorption to chemical conjugation.

From the technological perspective, the most attractive drug carriers are polymeric micelles formed by hydrophobic-hydrophilic block copolymers, with the hydrophilic blocks including PEO chains. These micelles have a spherical, core-shell structure, with the hydrophobic block forming the core of the micelle, while the hydrophilic PEO block (or blocks) forms the shell. Block copolymer micelles have promising properties as drug carriers in terms of their size and architecture. The advantages of polymeric micellar drug delivery systems over other types of drug carriers include: 1) long circulation time in blood; 2) appropriate size (10 to 30 nm) to escape renal excretion but to allow for the extravasaation at the tumor site; 3) simplicity in drug incorporation, compared to covalent bonding of the drug to the polymeric carrier and 4) drug delivery independent of drug character. [2]

The ability of PEO-coated particles to prohibit adsorption of proteins and cells depends on the surface density of PEO chains, their length and dynamics. [1,3] However, only a few known block copolymers form micelles in aqueous solutions. Among them, AB-type block copolymers, e.g. poly (L-aminoacid)-block-poly(ethylene oxide) [2,3–13] and ABA-type triblock copolymers. Triblock copolymers of this class are available under the name PLURONIC™, which shall be referred to generically herein as "P-triblock". P-triblocks are block polymers of PEO and PPO, usually triblock PEO-PPO-PEO copolymers, where PPO stands for poly(propylene oxide); the hydrophobic central PPO blocks form micelle cores, whereas the flanking PEO blocks form the shell, or corona which protects micelles from the recognition by RES. P-triblock copolymers are commercially available from BASF Corp. and ICI. P-triblock polymers are also disclosed in U.S. Pat. No. 5,516,703 to Caldwell et al, issued May 14, 1996, which is hereby incorporated by reference. P-triblock structure in aqueous solution have been extensively investigated by many authors and have been recently reviewed by Alexandridis [22], see also [16]. The phase state of P-triblock micelles can be controlled by choosing members of the P-triblock family with appropriate molecular weight, PPO/PEO block length ratio, and concentration. The hydrodynamic radii of P-triblock micelles at physiological temperatures range between 10 and 20 nm, which makes them prospects as potential drug carriers.

Recently the synthesis of the poly(ethylene oxide-block-isoprene-block-ethylene oxide) triblock copolymer has been reported [23]. Isoprene blocks comprising the core of this copolymer were crosslinked by UV irradiation, rendering micelles stable in the circulation system of mice.

The incorporation of drugs into block copolymer micelles may be achieved through chemical and physical routes. Chemical routes involve covalent coupling of the drug to the hydrophobic block of the copolymer leading to micelle-forming, block copolymer-drug conjugates. However, this approach involved complex synthetic steps and purification procedures. This concept is disclosed in Rigsdorf, et al. [24] and Kataoka, et al. [7–10, 25–27]

Physical entrapment is a better way of loading drugs into micellar systems. Physical entrapment of the anti-cancer drug doxorubicin (DOX) in micelles composed of poly (ethylene oxide-block-b-benzyl L-aspartate) has been disclosed by Kataoka, et. al. [12].

Polymeric surfactants at various aggregation state have been tested as drug carriers. P-triblock molecules in the uniimeric form (below the critical micelle concentration, CMC) were found to sensitize multi-drug resistant (MDR) cancerous cells. Kabanov and Alakhov [20, 28, 29] have found that there is a-dramatic increase in Daunorubicin and DOX cytotoxic activity toward the multi-drug resistant cell lines while in the presence of 0.01 to 1% of PLURONIC P85 or L61. The efficacy of the drug/P-triblock systems dropped above the CMC. It was concluded that the efficacy of P-triblockdelivery systems was based on the presence of P-triblock unimers.

The drop in the efficacy of drug/P-triblock systems above the CMC may be due to the substantial decrease in the intracellular drug uptake from dense P-triblock micelles. [30–32] The drug incorporated into the micelle core is masked from the external media by the corona composed of PEO chains.

This phenomenon may be used advantageously to prevent the unwanted drug interactions with healthy cells. However, the challenge is to ensure drug uptake at the tumor site.

The fundamental difference between using polymeric surfactants below or above the CMC is that below the CMC the enhanced intracellular uptake and enhanced cytotoxicity of the drug delivered with P-triblock unimers is exploited [20, 28, 29, 33], whereas above the CMC, the shielding properties of P-triblock micelles are used to prevent unwanted drug interactions with healthy cells. To ensure drug uptake from (or together with) polymeric micelles at the tumor site, micelle perturbation and cell membrane permeabilization by ultrasound is being proposed [30–32, 34].

Summarizing, drug delivery using micellar drug carriers proved to have many advantages over the use of free drugs.

Some micellar systems are structurally stable (these are micelles with solid-like cores that dissociate slowly at levels below their CMC, e.g. micelles formed by poly(L-aminoacid)-block-poly(ethylene oxide) copolymers [2, 5, 26]). As indicated by NMR data, molecular motion in the core of these micelles is substantially frozen. In contrast, P-triblock micelles or those formed by poly(ethylene oxide-block-isoprene-block-ethylene oxide) triblock copolymer dissociate very fast upon dilution [16]. These micelles have "soft" cores, which means that at room temperature theft molecular segments are above corresponding glass transition temperature, $T_g$ and move relatively fast. Since upon IV injections, the concentration of the polymeric drug carrier can drop to levels below the CMC, non-stable micelles require additional stabilization to be used in micellar form.

REFERENCES

1. S. I. Jeon, J. H. Lee, J. D. Andrade, p. (3. D. Gennes, J. Colloid Interface Sci. 142–158,(1991) 149–158.
2. K. Kamoka, O. S. Kwon, M. Yokoyarna, T. Okano, Y. Sakurai, I. Control. Release 24, (1993) 119–132.
3. J.-T. Li, K. D. Caldwell, N. Rapoport, Langmuir 10, (1994) 4475–4482.
4. S. Cammas, K. Kataoka, in *Solvents and Self-Organization of Polymers* S. E. Webber, Ed. (Kluwer Academic Pubi., Netherland, 1996) pp. 83–113.
5. M. Yokoyama, in Advances in *Polymeric Systems for Drug Delivery*. T. Okano, Ed. (Gordon and Breach Science Publishers, Iverdon, Switzerland, 1994) pp. 24–66.
6. M. Yokoyarna, Polymeric micelles for drug delivery: their stratagy and perspectives., 17th International Symposium on Recent Advantages in Drug Delivery Systems. 1995), pp. 99–102.
7. M. Yokoyama, T. Okano, Y. Sakurai, H. Ekimoto, C. Shibazaki, K. Kataoka, Cancer Res. 51, (1991) 3229–3236.
8. G. S. Kwon, M. Yokoyama, T. Okano, Y. Sakurai, K. Kataoka, Pharmac. Res. 10, (1993) 970–974.
9. G. Kwon, M. Naito, M. Yokoyama, Y. Sakurai, T. Okano, K. Kataoka, Langmuir 9, (1993) 1. S. I. Jeon, J. H. Lee, J. D. Andrade, p. (3. D. Gennes, J. Colloid Interface Sci. 142–158, (1991) 149–158.
10. G. S. Kwon, M. Yokoyama, T. Okano, Y. Sakurai, K. Kataoka, Enhanced tumor accumulation and prolonged circulation times of micelle-forming poly(ethylene oxide-co-aspartate) block copolymer-Adriamycin, conjugates., 6th International Symposium on Recent Advantages in Drug Delivery Systems 1993), pp. 175–176.
11. G. S. Kwon, K. Kataoka, Advanced Drug Delivery Reviews 16, (1995) 295–309.
12. G. S. Kwon, S. Suwa, M. Yokoyama, T. Okano, Y. Sakurai, K. Kataoka, Pharm. Res. 12, (1995) 192–195.
13. G. S. Kwon, M. Naito, K. Kataoka, M. Yokoyama, Y. Sakurai, T. Okano, Colloids and Surfaces B: Biointerfaces 2, (1994) 429–434.
14. A. V. Kabanov, E. V. Batrakova, N. S. Melik-Nubarov, N. A. Fedoseev, T. Y. Dorodnich, V. Y. Alakhov, I. R. Nazarova, V. A. Kabanov, I. Controlled Release 22, (1992) 141–158.
15. A. V. Kabanov, I. R. Nazarova, I. V. Astafieva, E. V. Batrakova, V. Y. Alakhov, A. A. Yaroslavov, V. A. Kabanov, Macromolecules 28, (1995) 2303–2314.
16. N. Rapoport, K. Caldwell, Colloids and Surfaces B: Biointerfaces 3, (1994) 217–228.
17. V. Yu. Alakhov, A. V. Kabanov, Expert Op Invest Drugs 7 (1998), 1453–1473.
18. E. V. Batrakova, T. Y. Dorodnych, E. Y. Klinskii, E. N. Kliushnenkova, O. B. Shemchukova, O. N. Goncharova, S. A. Aijakov, V. Y. Alakhov, A. V. Kabatiov, British Journal of Cancer 74, (1996) 1545–1552.
19. V. Y. Alakhov, E. V. Batrakova, T. Dorodnich, S. Li, A. Venne, A. V. Kabanov, Block copolymeric drug carriers: 1. delivery of antineoplastic drugs., First International Symposium on Polymer Therapeutics. (The School of Pharmacy, University of London, UK, London, 1996), pp. 213.
20. V. Alakhov, E. Moskaleva, E. Batrakova, A. Kabanov, Bioconjug. Chem. 7, (1996) 209–216.
21. N. Rapoport, in: 11th International Symposium On Surfactants In Solution. Jerusalem, Israel (1996), pp. 183.
22. P. Alexandridis, T. A. Hatton, Colloids and Surfaces A: Physicochemical and Engineering Aspects. 96, (1995) 1–46.
23. A. Rolland, J. O'Mullahe, P. Goddard, L. Brookman, K. Petrak, J. Appl. Polym. Sci. 44, (1992) 1195–1203.
24. K. Dorn, O. Hoerpel, H. Ringsdorf, in *Bioactive Polymer Systems* C. O. Gebelein, J. C. E. Canaher, Eds. (Plenum, New York, 1985) pp. 53 1–585.
25. M. Yokoyama, O. S. Kwon, M. Naito, T. Okano, Y. Sakurai, T. Seto, K. Kataoka, Bioconj. Chem. 3, (1992) 295–301
26. M. Yokoyama, T~Sugiyama, T. Okano, Y. Sakurai, M. Naito, K. Kataoka, Pharmac. Res. 10, (1993) 895–899.
27. M. Yokoyama, G. S. Kwon, T. Okano, Y. Sakurai, H. Ekimoto, K. Kataoka, In vivo antitumor activity of polymeric micelle-anticancer drug conjugates against murine C 26 tumor., 6th International Symposium on Recent Advantages in Drug Delivery Systems. 1993), pp. 177–178.
28. V. Y. Alakhov, E. Y. Moskaleva, E. V. Batrakova, A. V. Kabanov, Bioconj. Chem. 7, (1996) 209–216.
29. A. Venne, S. Li, R. Mandeville, A. Kabanov, V. Alakhov, Cancer Research 56, (1996) 3626–3629
30. N. Rapoport, N. Munshi, L. Pitina, W. G. Pitt, Polymer Preprints 38, (1997) 620–621.
31. N. Rapoport J. N. Herron, W. G. Pitt, and L. Pitina, Micellar Delivery of Doxorubicin and its Paramagnetic Analog, Ruboxyl to HL-60 Cells: Effect of Micelle Structure and Ultrasound on the Intracellular Drug Uptake. *J. Controlled Release*, 1999, 58: 153–162.
32. N. Munshi, N. Rapoport, W. O. Pitt, Cancer Letters 117, (1997) 1–7.
33. D. Miller, E. Batrakova, T. Waitner, V. Alakhov, A. Kabanov, Bioconjug. Chem. 8, (1997) 649–657.
34. N. Rapoport, A. Smirnov, A. Timoshin, A. M. Pratt, W. O. Pitt, Archives of Biochemistry and Biophysics 344, (1997) 114–124.
35. Ad. Smirnov and R. L. Belford, Archives of Biochemistry and Biophysics 362, (1999) 233–241.
36. Z. Zhou, B. Chu, J. Colloid Interface Sci. 126, (1988) 171–180.
37. W. Brown, K. Schillen, M. Almgren, S. Hvidt, P. Bahadur, J. Phys. Chem. 95, (1991) 1850.

38. W. B. Pratt, R. W. Ruddon, W. D. Ensminger, J. Maybaum, *Noncovalent DNA-Binding Drugs*. The Anticancer Drugs (Oxford University Press, New York Oxford, 1994).
39. N. M. Emanuel, O. N. Bogdanov, V. S. Orlov, Russian Chemical Reviews 53, (1984)1121–1138.
40. N. M. Emanuel, N. P. Konovalova, L. S. Povarov, A. B. Shapiro, e. al., Russian Academy of Sciences, 1 3-(1-oxyl-2,2,6,6-tetramethylpiperylidenyl4) hydrozone rubomycin hydrochloride with a paramagnetic center and a method of producing same (1982).
41. M. D. Bednarski, J. W. Lee, M. R. Callstrom, K. C. Li, Radiology 204, (1997) 263–268.
42. Rediske A. M., Rapoport N, Pitt W. G., Reducing bacterial resistance to antibiotics with ultrasound, *Letters in Applied Microbiology*, 1999, 28: 81–84.
43. S. Stolnic, L. Illum, Davis, S. S., Long circulating microparticulate drug carriers. *Advanced Drug delivery Reviews*, 1995, 16:195–214.
44. Hoffman, A. S., Environmentally sensitive polymers and hydrogels: "smart" biomaterials. MRS Bulletin, 1991, 42–45
45. Kost, J., Langer, R., Responsive polymer systems for controlled delivery of therapeutics. *Trends in Biotechnology*, 1992, 10: 127–131
46. Lee, P. I., in controlled Release Technology: *Pharmaceutical Application.*, Ed., P. I. Lee, W. R. Good. 1987, ACS, Washington, vol. 348, pp. 71–83.
47. Peppas, N. A., *Hydrogels in Medicine and Pharmacy*. Ed., AEds., N. A. Peppas, R. W. Korsmeyer, 1987, CRC Press, Boca Raton, vol. 3.
48. Siegel, R. A., in *Pulsed and Self regulated Drug Delivery.*, Ed., AEds. J. Kost. 1990, Boca Raton, pp. 129–157.
49. Park, T. G., Hoffman, A S., Synthesis and characterization of pH- and/or temperature-sensitive hydrogels. *J. Appl. Polymer Sci.*, 1992, 46:659–671
50. Kim, Y.-H., Kwon, I. C., Bae, Y. H., Kim, S W., Saccharide effect on the lower critical solution temperature of thermosensitive polymers. *Macromolecules*, 1995, 28:939–944
51. Kataoka, K., Koyo, H., Tsuruta, T., Novel pH-sensitive hydrogels of segmented poly(amine ureas) having a repetitive array of polar and apolar units in the main chain. *Macromolecules*, 1995, 28:3336–3341.
52. Jin, M. R., Wu, C F., Lin, P. Y., Hou, W., Swelling of and solute exclusion by poly(Nalkylacrylamide) gels. *J. Appl. Polym. Sci.*, 1995, 56:285–288.
53. Chytry, V., Netopilik, M., Bohdanecky, M., Ulbrich, K., Phase transition parameters of potential thermosensitive drug release systems based on polymers of N-alkylmethacrylamides. *L. Bionialer. Sci. Polymer Edn.*, 1997, 8:817–824.
54. Feil, H., Bae, Y. H., Feijen, J., and Kim, S. W., Effect of Comonomer Hydrophilicity and Ionization on the Lower Critical Solution Temperature of N-Isopropylacrylamide Copolymer& *Macromolecules*, 1993, 26:2496–2500.
55. Chen, M. -Q., Kishida, A., and Akashi, M., Graft Copolymers Having Hydrophobic Backbone and Hydrophilic Branches. XI. Preparation and Thermosensitive Properties of Polystyrene Microspheres Having Poly(N-isopropylacrylamide) Branches on Their Surfaces, *Journal of Polymer Science: Part A: Polymer Chemistry*, 1996, 34:2213–2220.
56. Idziak, I., Avoce, D., Lessard, D., Gravel, D., and Zhu, X. X., Thermosensitivity of Aqueous Solutions of Poly~N,N-diethylacrylamide). *Macromolecules*, 1999, 32: 1260–1263
57. Vernon, B., Gutowska, A., Kim, S W., and Bae, Y. H., Thermally Reversible Polymer Gels for Biohybrid Artificial Pancreas. *Macromol. Symp.*, 1996, 109:155–167.
58. Vakkalanka, S K., Brazel, C S., Peppas, N. A., Temperature- and pH-sensitive terpolymers for modulated delivery of streptokinase. *J. Bio mater. Sd. Polym. Ed.*, 1996, 8:119–129.
59. Stayton, P. S., Shimoboji, T., Long, C., Chilkoti, A., Chen, G., Harris, J. M., Hoffman, A. S., Control of protein-ligand recognition using a stimuli-responsive polymer. *Nature*, 1995, 378:472–474.
60. Jeong, B., Bae, Y. H., Lee, D. S., Kim, S. W., Biodegradable block copolymers as injectable drug-delivery systems. *Nature*, 1997, 388:860–862.
61. Chandehari, H., Kopeckova, P., Kopecek, J., In vitro degradation of pH-sensitive hydrogels containing aromatic azo bonds. *Biomaterials*, 1997, 18:861–872.
62. Chiu, H-C., Kopeckova, P., Deshmane, S. S., Kopecek, J., Lysosomal degradability of poly(a-amino acids). *J. Biotned. Mater Res.*, 1997, 34:381–392.
63. Leroux, J. C., *J. Biotned. Mater Res.*, 1994, 28:471–481.
64. Kataoka, K., Kwon, G. S., M. Yokoyama, Okano, T., Sakurai, Y., Block copolymer micelles as vehicles for drug delivery. *J. Control. Release*, 1993, 24: 119–132.
65. Yuan, F., Leuning, M., Huang, S. K., Berk, D. A., Papahadjopulos, D., Jam, R. K., Microvascular permeability and interstitial penetration of sterically-stabilized (stealth) liposomes in human tumor xenograft. *Cancer Res.*, 1994, 54:3352–3356.
66. Kwon, G. S., Suwa, S., Yokoyama, M., Okano, T., Sakurai, Y., Kataoka, K., Enhanced tumor accumulation and prolonged circulation times of micelle-forming poly(ethylene oxideaspartate) block copolymers-adriamicin conjugates. .1. *Contr Release*, 1994, 29:17–23.
67. A. V. Kabanov and V. Yu. Alakhov, Micelles of amphiphilic block copolymers as vehicles for drug delivery in: Amphiphilic Block Copolymers: Self Assembly and Applications, Ed. P. Alexandridis and B. Lindman. Elsevier, Netherland, 1997
68. N. Y. Rapoport, Stabilization and Acoustic Activation of Pluronic Micelles for Tumor-Targeted Drug delivery. Colloids and Surfaces B: Biointerfaces 16 (1999) 93–111
69. Tian, M., Qin, A., Ramireddy, C., Webber, S., Munk, P., Hybridization of block copolymermicelles. *Langmuir*, 1993, 9:1741–1748
70. Emanuel, N. M., Konovalova, N. P., Dyachkovskaya, R. F., Potential anti-cancer agents-nitroxyl derivatives of Rubomicin. *Neoplasma*, 1985, 32: 285–292.
71. Konovalova, N. P., Dyachkovskaya, R E., Ganieva, L. K., Volkova, L. M., lapshin, I. M., Rudakov, B. Y., Shaposhnikov, Y. G., Shapiro, A. B., Subrenal capsule assay of human tumor chemosensitivity. 1991, 38:275–284.
72. Rapoport, N., Pitina, L., Intracellular distribution and intracellular dynamics of a spin-labeled analog of doxorubicin by fluorescence and EPR spectroscopy. J. Pharm. Sci., 1997, 87:321-325.

73. Domb, A. J., Langer, R., Polyanhydrides: 1: Preparation of high molecular weight polymers. *J. Polym. Sci., A, Polym. Chem.*, 1987, 25:3373–3386.

74. Domb, A. J., Nudelman, R., in vivo and in vitro elimination of aliphatic polyanhydrides. *Biomateriabs*, 1995, 16:319–323

75. Barrett, A. J., Heath, M. F., in Lysosomes: A laboratory handbook, Ed. J. T. Dingle. 1977, Elsevier, Amsterdam, pp. 19–145.

76. G. S. Kwon and K. Kataoka, Block Copolymer Micelles as long circulating drug-vehicles. Advanced Drug Delivery Reviews 16 (1995) 295–309.

77. G. S. Kwon, M. Naito, M. Yokoyama, T. Okano, Y. Sakurai, and K. Kataoka, Block copolymer micelles for drug delivery: loading and release of doxorubicin. J. Control. Release 48 (1997) 195–201.

78. M. E. Johnson et al. J. Pharm Sci. 85 (1996) 670–677.

79. K. Tachibana, T. Uchida, K. Ogawa, N. Yamashita, and K. Tamura, Induction of cell-membrane porosity by ultrasound. Lancet 353 (1999) 1409.

80. J. Liu, T. N. Lewis, and M. R. Prausnitz, Non-invasive assessment and control of ultrasound mediated membrane permeabilization. Pharm. Res. 15 (1998) 918–924.

81. C. L. Christman, A. J. Carmichael, M. M. Mossaba, and P. Riesz, Evidence for free radical produced in aqueous solutions by diagnostic ultrasound. Ultrasonics 25 (1987) 31–34.

82. N. Y. Rapoport, A. I. Smimov, Interactions of spin-labeled anthracyclin with DNA, proteins and lipid bilayers: an electron paramagnetic resonance study, submitted to Archives Biochem. Biophys., 2000.

83. S. Mitragotri, D. Blankschtein, and R. Langers, Transdermal drug delivery using low-frequency sonophoresis. Pharm. Res. 13 (1996) 411–420.

84. P. Alexandridis, J. F. Holzwarth, and T. A. Hattons, Micellization of Poly(ethylene oxide)-Poly(propylene oxide)-Poly(ethylene oxide) Triblock Copolymer in Aqueous Solutions: Thermodynamics of Copolymer Association. Macromolecules 27 (1994) 2414

Objects of the Invention

It is, therefore, an object of the invention to provide a system for the stabilization of micelles.

Another object of the invention is to provide a system for activation of stabilized micelles.

It is further an object of the invention to provide a system for drug delivery by the stabilization and activation of micelles.

Further objects of the invention will become evident in the description below.

BRIEF SUMMARY OF THE INVENTION

The present invention involves various routes of micelle stabilization against degradation upon dilution. The invention also involves the effect of ultrasound on drug release from micelles and drug uptake by cancerous cells. In practice of the present invention, a drug can be encapsulated in a long-circulating micelle. Extravasation proceed only at tumor sites due higher permeability of blood vessels, and is enhanced by ultrasound. The micelle-encapsulated drug is accumulated at the tumor site. The uptake of the micelle-encapsulated drug is enhanced by ultrasound.

The advantages of the micelle drug carriers of the invention included long circulation time in the blood, appropriate size to escape renal excretion, appropriate size to allow for extravasation at the tumor site, and simplicity of drug loading. In addition, sterilization is possible by filtration, and micelles can be introduced by intravenous injections.

The micelles are formed from any suitable micelle forming block copolymer, including AB-type, and ABA-type. Exemplary micelle forming block polymers are the, polymers of the P-triblock family.

To be used as drug carriers, P-triblock micelles require stabilization to prevent degradation caused by significant dilution accompanying IV injection. Three routes of P-triblock micelle stabilization are included in the present invention The first route is direct radical crosslinking of micelles cores which results in micelle stabilization.

In the second method, a small concentration of an oil, such vegetable oil (about 0.0005 percent)is introduced into diluted P-triblock solutions. This substantially decreases micelle degradation upon dilution while not compromising drug loading capacity of oil-stabilized micelles. The amount oil used is much small than that required to form an emulsion, which is about 1 percent. The oil bonds or interacts with the core to make it more hydrophobic and stable, but it is insufficient to form an emulsion of the oil in water.

The third route is a technique based on polymerization of the temperature-responsive LCST hydrogel in the core of P-triblock micelles. The hydrogel phase is in a swollen state at room temperature, which provided for a high drug loading capacity of the system. The hydrogel collapses at physiological temperatures which locked the core of micelles thus preventing them from fast degradation upon dilution. This new drug delivery system is referred to herein as "P-gel". Phase transitions in P-gel caused by variations in temperature or concentration were studied by the EPR.

The effect of P-triblock concentration in the incubation medium on the intracellular uptake of two anti-cancer drugs was studied. At low P-triblock concentrations, when the drugs were located in the hydrophobic environment, drug uptake was increased, presumably due to the effect of a polymeric surfactant on the permeability of cell membranes. In contrast, when the drugs were encapsulated in the hydrophobic cores of P-triblock micelles, drug uptake by the cells was substantially decreased. This may be used advantageously to prevent undesired drug interactions with normal cells. Ultrasonication enhanced intracellular drug uptake from dense P-triblock micelles. These findings permitted the formulation of a new concept of a localized drug delivery.

An advantage is that the p-gel micelles are stable for drug delivery, but not so stable that they cannot be degraded by the body. After a matter of weeks, the stabilized p-gels will gradually destabilize. This allows sufficient time to function effectively as a drug delivery system, but the degradation will allow eventual removal from the body. This is unlike many drug delivery systems that involve stable components that are slow to be removed from the body. The thermodynamics of the p-gel system direct the system toward dissolution, and instability, but the kinetics are very slow.

Another aspect of this embodiment is the use of hydrogels that are stimuli responsive to other environmental states, such as pH.

Other substances that are introduced into the body, other than drugs, can be encapsulated and delivered by the stabilized micelle system of the invention.

Ultrasound Release

Another aspect of the invention is the use of pulsed ultrasound to release an encapsulated drug. In particular, for hydrogel stabilized micelles, the release of drug by ultrasound is reversible, with allows a highly controlled release of drug using a pulsed ultrasound system.

DETAILED DESCRIPTION OF THE INVENTION

EXAMPLES

Manufacture of Stabilized Micelles

Figure 1A:
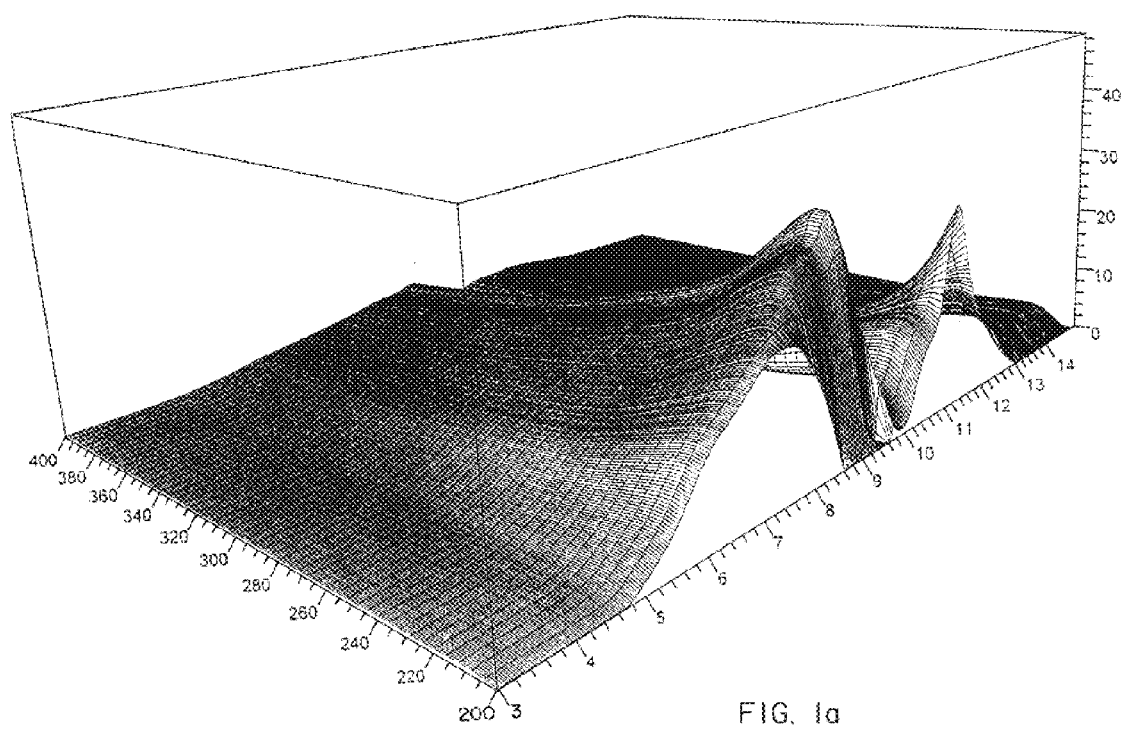
FIGS. 1a, 1b, 1c. 1. 3-dimensional size exclusion chromatograms of P-triblock samples: x-axis—retention time, mm; y axis—wave length, nm; z-axis—absorption. Concentration of the injected polymer 1 wt %; eluent—water, detector: UV diode array; injection volume 10 μl; temperature 30° C. (a) control P-triblock sample, (b) and (c) crosslinked samples using 5 wt % (b) and 10 wt % (c) of benzoyl peroxide in P-triblock Micelles.

P-triblock PLURONIC P-105 micelles were chosen as a model polymeric micellar system. The rational behind the choice of P-triblock was that P-triblock can form unimers, loose water penetrated aggregates, and micelles with hydrophobic cores, and the phase state of the drug carrier can be controlled by choosing members of the P-triblock family with appropriate molecular weight, PPO/PEO block length ratio, and concentration. The phase state of P-triblock solutions can be characterized by the Electron Paramagnetic Resonance technique (EPR) [16]. In addition, reports have indicated that P-triblock solutions in concentration below 1 wt % are non-toxic [14].

The hydrodynamic radii of P-triblock micelles at physiological temperatures range between 10 and 30 nm, which makes them prospective drug carriers.

Experimental Methods

Materials

P-triblock P-105 with an average molecular weight of 6,500, the number of monomer units in PEO and PPO segments being respectively 37 and 56, was supplied by BASF Corporation and used as received. Spin probe 16-doxylstearic acid (16-DS) was purchased from Sigma, St. Louis, Mo. Monomers, crosslinkers, radical initiators were purchased from Polysciences, Inc., Warrington, Pa.

Cells

HL-60 promyelocytic cell line was provided by Dr. Murray (Brigham Young University, Provo, Utah), They were cultured in RPMI 1640 medium supplemented with 20% fetal calf serum, 2 mM L-glutamine, 0.2% sodium bicarbonate and 50 $\mu$g/ml gentamicin at 37° C. in humidified air containing 5% $CO_2$.

Drugs

Ruboxyl (Rb) was provided by Dr. Shapiro (Institute of Biochemical Physics, Moscow, Russia). DOX was supplied by the University Hospital, University of Utah, Salt Lake City, Utah, USA).

Incubation Media

Cells were incubated with the drug in the RPMI medium or PBS in the absence or presence of P-triblock P 105. P-triblock was dissolved at 0.1, 1.0, 10, or 20 wt % in RPMI media or PBS and the solutions obtained were sterilized by filtration through a 0.2 um filter.

Size Exclusion Chromatography

Size exclusion chromatography was performed on a Spherogel TSK 6000PW (Beckman Co), with water as a mobile phase (flow rate of 1 ml/mm at 30° C.); injection volume was 10 $\mu$l. Hewlett Packard Series 1100 Liquid Chromatograph equipped with multi-wavelength detector was used, which allowed to measure absorption of analytes in the range of 190–400 nm. The column was calibrated using PEG standards. Before the experiment, control and crosslinked P-triblock samples were diluted to the final P-triblock concentration of 1% w/v.

Measuring Loading Capacity of Micelles

A dry powder of the EPR probe (16-DS) was incubated with unstabilized or stabilized micellar solutions of P-triblock for 15 mm under constant shaking. Unsolubilized probe was removed by centrifugation. The concentration of a solubilized probe was measured by the EPR. The same technique of probe introduction was used for pyrene. Water solubility of 16-DS or pyrene is very low and can be neglected. Dissolved probes are associated with P-triblock molecules and thus reflect the loading capacity, dynamics and environment of the latter. For a fluorescent drug, Rb, the same concentration of Rb (20 $\mu$g/ml) was introduced into non-stabilized and stabilized micellar P-triblock solutions at 37° C. from a stock solution. Because fluorescence of Rb within P-triblock micelles is much higher than outside micelles [31], the fraction of the drug within micelles can be estimated as $$F_{mes} = a_m F_m + (1-a_m) F_s$$

where Fmes is a measured fluorescence intensity, $F_m$ is Rb fluorescence intensity when all the drug is localized in the hydrophobic core of micelles (measured in a 20% P-triblock solution at 37° C.), $F_s$ is fluorescence intensity in non-micellar solutions (i.e., in PBS), and $a_m$ is the fraction of the drug located in the hydrophobic core of micelles.

Spin Probe Introduction

A 16-DS spin probe was introduced into P-triblock solutions in the following manner: an aliquot of a stock solution of 1 6-DS in ethyl alcohol was placed at the bottom of a test tube; alcohol was evaporated in the air stream, upon which P-triblock solutions of various concentrations were added. The samples were sonicated for 15 mm to enhance spin probe solubilization.

EPR Experiments

The samples were placed in the EPR capillaries or flat EPR cells (Wilmad Glass Corporation, Buena, N.J.). EPR spectra were acquired in a Bruker (Billerica, Mass.) ER-200 SRC X-band EPR spectrometer (installed at the University of Utah) or Varian (Palo Alto, Calif.) Century Series E-112 X-band spectrometer in the Illinois EPR Research Center (University of Illinois at Urbana-Champaign). Incident microwave power was set to 0.5–2 mW to avoid saturation. Modulation frequency was 100 kHz, modulation amplitude was a quarter of a line width. EPR spectra were recorded at room temperature and at 37° C. The EPR spectra were taken sequentially, digitized, and stored with the aid of a commercial EPR software/hardware package (Scientific Software Services, Bloomington, Ill.).

Double integrals of individual EPR signals are proportional to the corresponding spin concentrations. Hyperfine splitting of spectral lines characterizes the hydrophobicity of a probe environment; signal shape (pick-to-pick line width, low-field to high-field line intensity ratio) is used to measure probe motion parameters (rotational correlation time, $t_r$, anisotropy of motion etc.). Lorenzian component of the line shape and double integrals of the spectra were measured by fitting of each spectrum to the inhomogeneous line shape model using a computer program described in [35]. This program provides for the separation of overlapping EPR signals. All spectra were processed in automatic mode, in which the best-fit parameters for the spectrum were used as an initial approximation for the Levenberg—Marquard optimization of the next spectrum in the sequence.

Dynamic Light Scattering

Dynamic light scattering was measured using a BI 200 Spectrometer from Brookhaven Instruments equipped with a BI 2030 AT 72-channel autocorrelator. DSC data were analyzed using a BI30AT program.

Insonation

Ultrasound was generated by a Sonicor SC 100 sonication bath operating at 67 kHz and 37° C. Power density was controlled by adjusting the input voltage and was measured with a hydrophone.

Measuring Drug Uptake by the Cells

Intracellular uptake of DOX and Rb was measured using a fluorescence technique, in which compounds were excited at 488 nm and technical emission spectra were recorded between 510–700 nm. Two sets of samples were studied, one incubated and another sonicated. For the first set (incubated), the cells were incubated at 37° C. with DOX or Rb, which were either dissolved in the RPMI medium (or PBS), or the drugs were solubilized in P-triblock PLURONIC P-105 solutions of various concentrations. For the second set of samples, the cells were sonicated by 70 kHz ultrasound at 379C up to 1 hour in the presence of drug to assess the, effect of ultrasound on the drug uptake from molecular and micellar solutions. After being incubated/sonicated with and without the drug, the cells were spun out, washed twice with cold PBS, and re-suspended in PBS. Sonication power density was maintained at or below 2.4 W/cm$^2$. No immediate cell death caused by sonication was observed. Sonication in the absence of P-triblock did not, affect cell proliferation. Because drug fluorescence within the cells was substantially quenched, drug uptake was quantified in cell lysates; cells were lysed by incubating them with 1 wt % SDS solution for 1–2 hat 37° C. This process transferred the drug from cellular, components to SDS micelles. Calibration experiments showed a linear dependence of Rb or DOX fluorescence intensity on concentration in 1% SDS solutions in the concentration range of interest. Upon the completion of cell lysis, fluorescence spectra of the lysates were recorded. To quantify the concentration of lysed cells, cell lysates were filtered through 0.2 mm filters, and their optical density was measured by protein absorption at 280 nm (OD 280 nm). Calibration experiments showed a linear dependence of OD 280 nm on the concentration of lysed cells. The fluorescence intensity of lysates was normalized by OD 280 nm. In parallel, the depletion of the drug from the incubation medium was measured by the decrease of supernatants' fluorescence.

Results and Discussion

Micelle Stabilization Against Degradation Upon Dilution

Direct Radical Crosslinking

At low temperatures and/or concentrations, P-triblock exists in aqueous solutions as individual coils, or unimers, with a size of approximately 1–2 nm [36]. Upon increasing temperature and/or concentration, the transition proceeds from unimers to loose, water penetrated aggregates to micelles with hydrophobic cores. Micelle cores consist of PPO blocks. Upon dilution below the CMC, these micelles dissociate into loose, multimolecular aggregates or unimers within minutes. (See Rolland [23].)

This experiment shows that radical crosslinking of P-triblock micelle cores will prevent micelle dissociation. The crosslinking procedure is designed to confine the crosslinking to micelle cores without compromising the structure and dynamics of the PEO side chains. For that, a hydrophobic radical initiator was chosen, benzoyl peroxide, that dissolves predominately in the micelle core. The initiator at the concentration range of 0.5 to 20 mg/ml (which corresponds to 0.25 wt %–10 wt % in respect to P-triblock) Was introduced, into 20% P-triblock PLURONIC P-105 solution under sonication (30 sec, 70 kHz). The solution was degassed and the crosslinking was performed by heating at 60° C. for 24 hours. Micelle stabilization upon dilution was tested by size exclusion chromatography.

The chromatograms of non-crosslinked samples manifested two major peaks at retention times of 7.6 and 11.4 mm and a very weak-peak at 9.2 mm (FIG. 1a and Table 1). UV-spectra of all spectra components were in the wavelength area of polyethers' absorption (190–210 nm). UV spectrum of the first peak had a long tail extending to 400 nm. It is speculated that this peak belongs to swollen multimolecular aggregates and that a long tail in UV spectra of these components results from light scattering.

For the third peak, no tails beyond 210 nm were observed. This peak presumably belongs to unimers and characterizes the molecular weight distribution of the initial polymer that is found rather broad (corresponding to molecular weights from 600 D to 23,000 D, with a maximum at 7,000 D, which is close to .6,500 D reported for P-triblock PLURONIC P105 by the manufacturer).

Figure 1B:
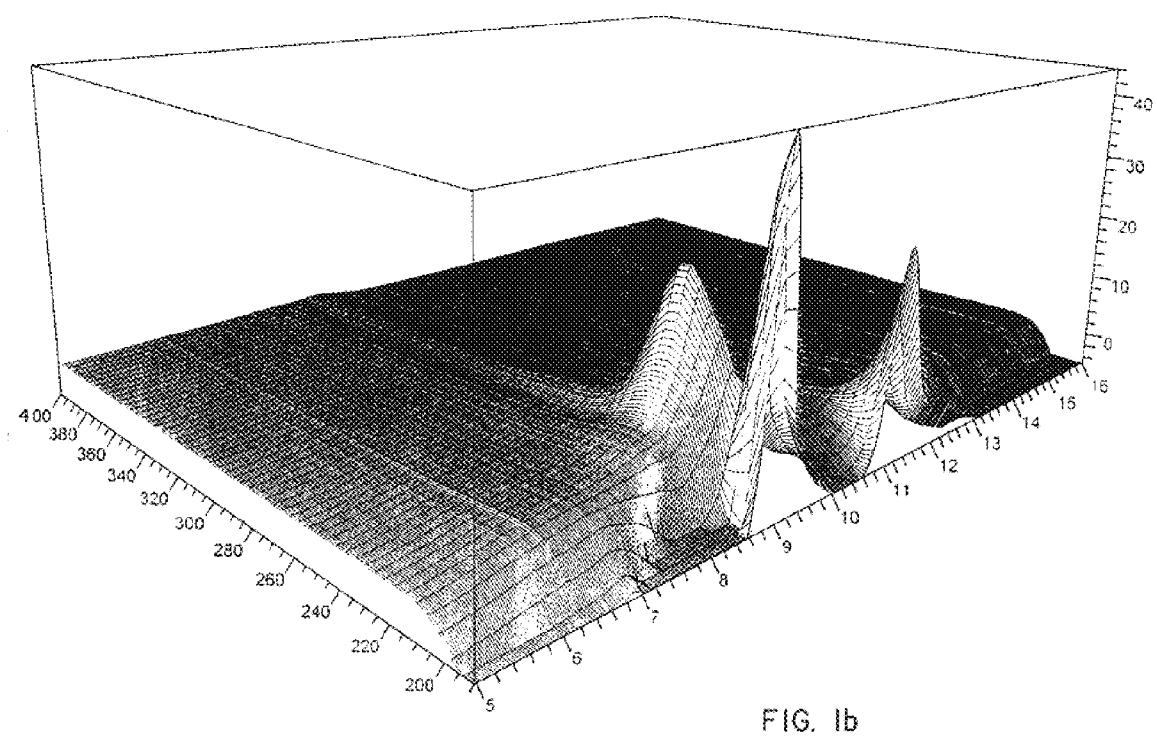
Figure 1C:
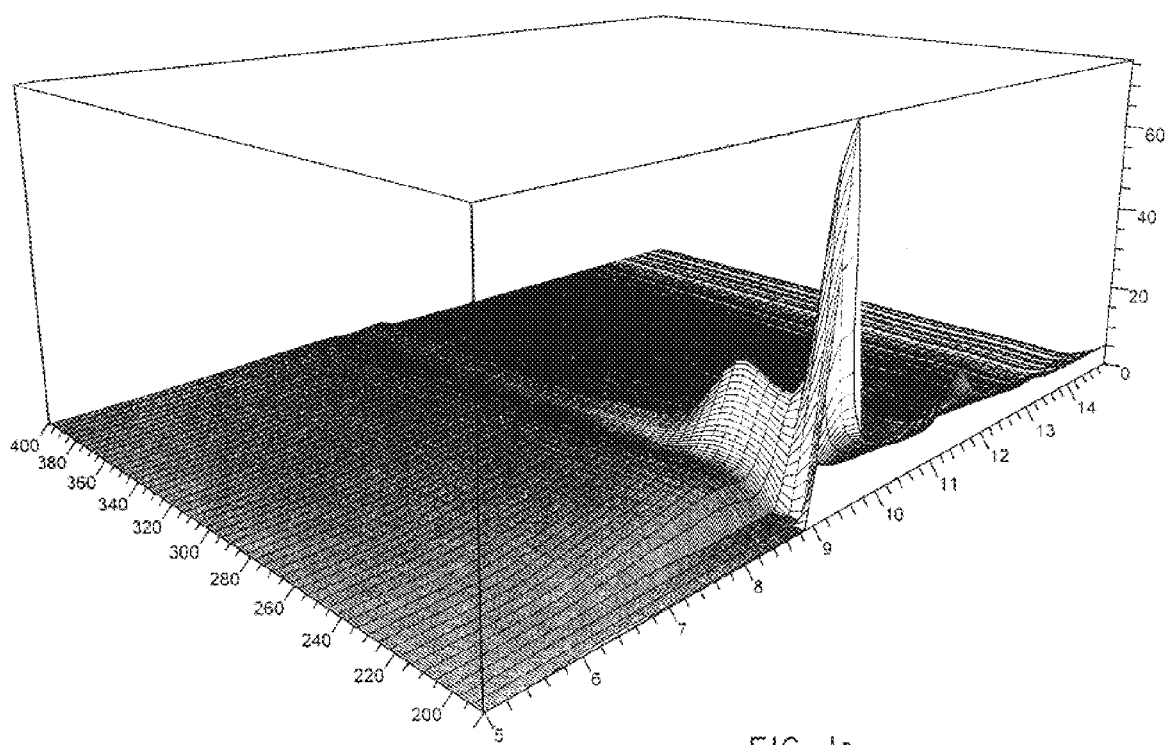

The chromatograms of crosslinked samples manifested all three peaks characteristic of the control non-crosslinked sample. However, the ratio of peak area changed dramatically upon crosslinking, a peak at a retention time of about 9.0–9.3 mm becoming the strongest (FIG. 1b). The area of this peak substantially increased (to about 80% of total) upon increasing initiator concentration, while areas of the first and the third peak dropped. UV spectra manifested a presence of benzoyl peroxide in the component corresponding to the strong second peak (absorption at 226 nm, FIGS. 1b and 1c). This implies that the second peak belongs to P-triblock micelles stabilized by radical crosslinking. The concentration of crosslinked micelles grew with the concentration of benzoyl peroxide (Table 1).

TABLE 1

Parameters of (PC peaks for non-crosslinked and crosslinked P-triblock P-105 samples.

| Sample | Relative peak area (%'/Retention time (min' | | |
|---|---|---|---|
| Control | 56/7.6 | 5/9.2 | 39/11.4 |
| Crosslinked~1* | 30/7.7 | 44/9.0 | 26/11.3 |
| Crosslinked~2* | 9/7.5 | 78/9.3 | 13/11.4 |

*The concentration of benzoyl peroxide was 5 wt % of P-triblock for a crosslinked-1 sample and 10 wt % of P-triblock for a crosslinked-2 sample.

Introduction of Low Concentrations of Vegetable Oil

The rationale behind this approach was that increasing hydrophobic interactions in the micelle core should result in decrease in the CMC and thus prevent micelle degradation upon dilution. In these experiments the EPR technique was used to characterize micelle formation and degradation. This technique has been successfully used to study the micellization of various members of P-triblock copolymer family in aqueous solutions [16] and dynamics of P-triblock-coated polymeric colloids [3].

The spin-probe EPR technique provides the following information on the system: solubilization efficiency (the concentration of a solubilized probe measured by the double integral of the spectral line), polarity of the probe environment (characterized by the hyperfine splitting constant, $a_N$), the microviscosity of the probe environment (characterized by the rotational correlation time, $t_{rot}$), and local concentrations of the probe (characterized by the line width or a shape of the spectrum at 77K).

Figure 2:
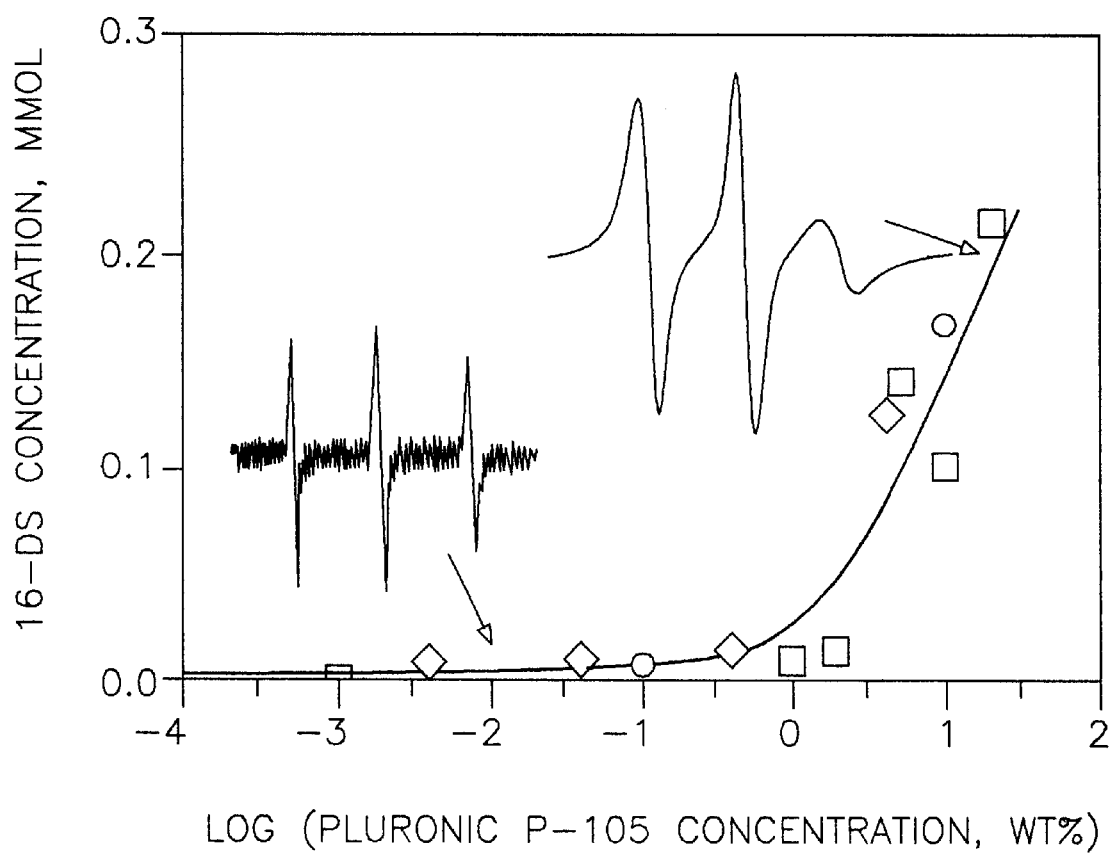
FIG. 2. The concentration of a solubilized 16-DS vs. P-triblock PLURONIC P405 concentration in aqueous solutions. The EPR spectra are shown for 16-DS in a 0.01 wt % (lower spectrum) and 10 wt % P-triblock solution (upper spectrum) at room temperature.

Formation of P-triblock micelles resulted in dramatic changes of EPR spectra of a solubilized spin probe, 16-DS (FIG. 2). This probe has an amphiphilic character; two polar groups, namely carboxyl and nitroxide groups, are separated by a long fatty chain. The probe does not spontaneously dissolve in water; dissolved probe molecules are associated with P-triblock molecules and thus reflect the loading capacity, dynamics and environment of the latter. Probe "solubility" in micellar solutions is much higher than that in unimeric solutions (see FIG. 2), which allows the probe to accurately report the onset of micelle formation.

Figure 3:
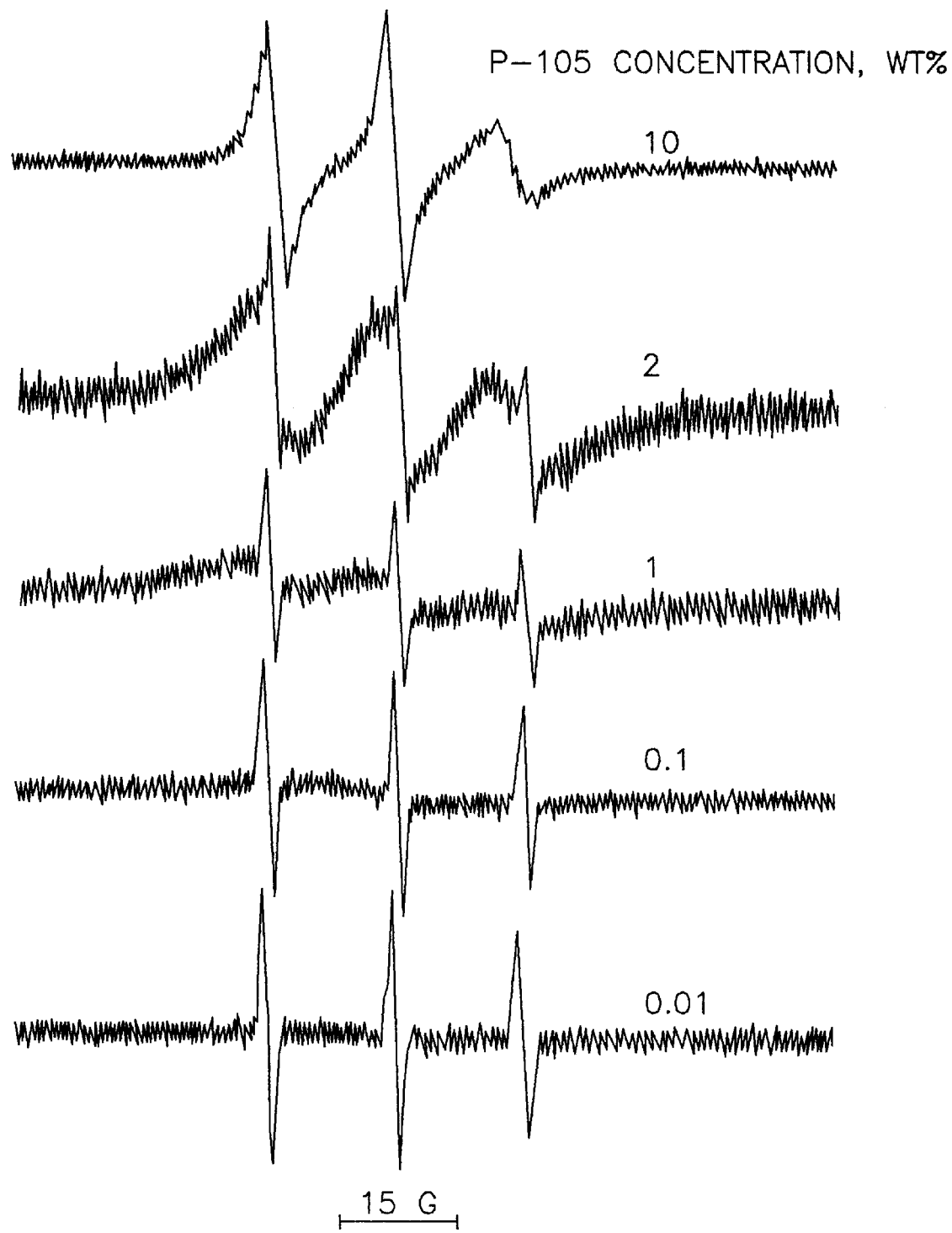
FIG. 3. The EPR spectra at room temperature of 16-DS in control P-triblock solutions of progressively decreasing concentrations.

EPR spectra of solubilized nitroxide probes are presented by three-line signals; line shape (hyperfine splitting constant $a_N$, peak-to-peak amplitude ratio, line width) reports hydrophobicity and microviscosity of the probe environment. Differences in the EPR spectra of a 16-DS probe solubilized in P-triblock P-105 solutions of various concentrations indicated probe transition from the hydrophilic environment of P-triblock unimers (FIG. 3, lower spectrum) to the hydrophobic environment of cores of P-triblock micelles (FIG. 3, upper spectrum; see also FIG. 2). At a very low P-triblock PLURONIC P-105 concentration corresponding to P-triblock unimers (0.001 wt %), one P-triblock molecule was associated with several 16-DS molecules, which were located in the hydrophilic environment. Upon increasing P-triblock concentration up to 0.1% at room temperature, several P-triblock molecules corresponded to the solubilization of one probe molecule; the probe was still located in the hydrophilic environment; which system is called "loose aggregates". Finally, at P-triblock concentrations of 1 wt % or higher, EPR spectra showed probe transfer into the hydrophobic environment indicating the formation of P-triblock micelles with hydrophobic cores [16]. The EPR spectra presented in FIG. 2 and FIG. 3 indicated that the microviscosity of the interior of P-triblock micelles was substantially higher than that outside micelle cores; they also showed a dramatic increase of P-triblock solubilization efficiency for lipophilic substances upon the onset of the formation of micelles with hydrophobic cores.

For the oil-stabilized micelles, oil (1% v/v) was introduced into a 20% (w/v) P-triblock solution together with a spin probe, 16-DS; the sample was sonicated for 15 mm, upon which sequential dilutions were done to the final P-triblock concentrations of 10%, 2%, 1%, 0.1% and 0.01%. In parallel, sequential dilutions were made to the control sample that did not comprise oil.

Figure 4:
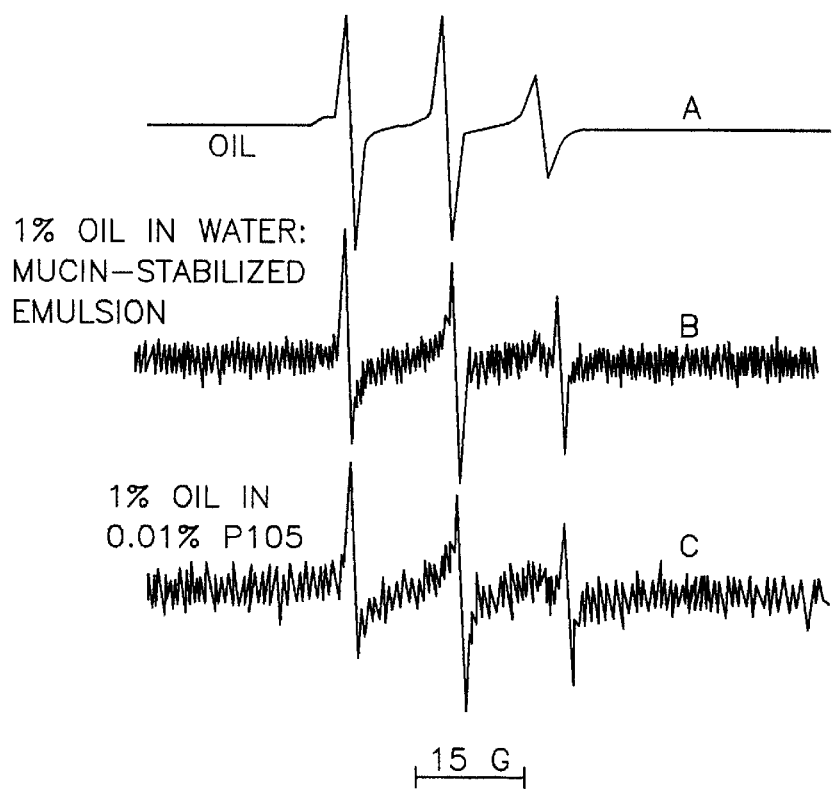
FIG. 4. The EPR spectra at 37° C. of 16-DS dissolved in oil (spectrum A), solubilizedin 1% oil-in-water emulsion stabilized by 0.01% P-triblock PLURONIC P-105 (spectrum B), and solubilized in 1% oil-in-water emulsion stabilized by mucin (spectrum C).

The EPR spectra of 16-DS dissolved in oil (spectrum A) or solubilized in oil-in-water emulsions stabilized with a surface active protein, mucin (B) are presented in FIG. 4.

The shape of the spectrum of 16-DS solubilized in a 10% P-triblock PLURONIC P-105 solution (FIG. 3, upper spectrum)as well as that of a probe dissolved in oil (FIG. 4, upper spectrum) is characteristic of a nearly isotropic probe motion in a viscous hydrophobic medium. Values of hyperfine splitting constants $a_N$ indicate that oil is more hydrophobic than a core of P-triblock micelles ($a_N$=14.270 for 16-DS in oil to be compared to 14.60 for a probe in a 10% P-triblock-solution).

For control samples, the shape of spectral lines changed dramatically upon progressive dilutions indicating micelle degradation.

In 10% P-triblock solution, at room temperature, the probe was localized exclusively in the hydrophobic core of P-triblock micelles ($a_N$=14.6 0). Upon a 5-fold dilution of this sample, a very small populations of the probe located in the hydrophilic environment was revealed (about 1% of the total probe), indicating the onset of micelle degradation. (Spectra simulations-were done using the EWVoigt software [Peef(Philip D., II) Morse, Scientific Software Services, P.O. Box 406, Normal, Ill. 61761-0406].) This conclusion is based on the following consideration: since the probe is always associated with P-triblock molecules, the concentration ratio of the probe in the hydrophobic and hydrophilic environment reflects the ratio of micelle-encapsulated and unimer-associated (or loose aggregates-associated) probe. In diluted solutions, EPR spectra manifested the superposition of the lines corresponding to the probe localized in the hydrophobic environment of micelle cores (broad lines with $a_N$=14.60) and in the hydrophilic environment of unimers or loose aggregates (sharp lines with $a_N$=15.9 0). The population of the probe in the hydrophilic environment grew with dilution. Only traces of micelles were observed in 0.1% solutions (a broad single line that appears as a background of a three-line signal for 0.1% P-triblock concentration is characteristic of a very high local concentration of the probe in a small number of micelles). No micelles manifested themselves in 0.01% solutions, which means that this concentration was below the CMC; the probe was located exclusively in the hydrophilic environment characterized by $a_N$=16.00; a sharp three-line spectrum pointed to fast tumbling.

When 1% v/v oil was introduced into a 0.01% P-triblock solution, a typical oil-in-water emulsion was formed (compare the second and the third spectrum of FIG. 4) indicating that at this P-triblock-to-oil ratio, P-triblock stabilized oil-in-water emulsions.

Figure 5:
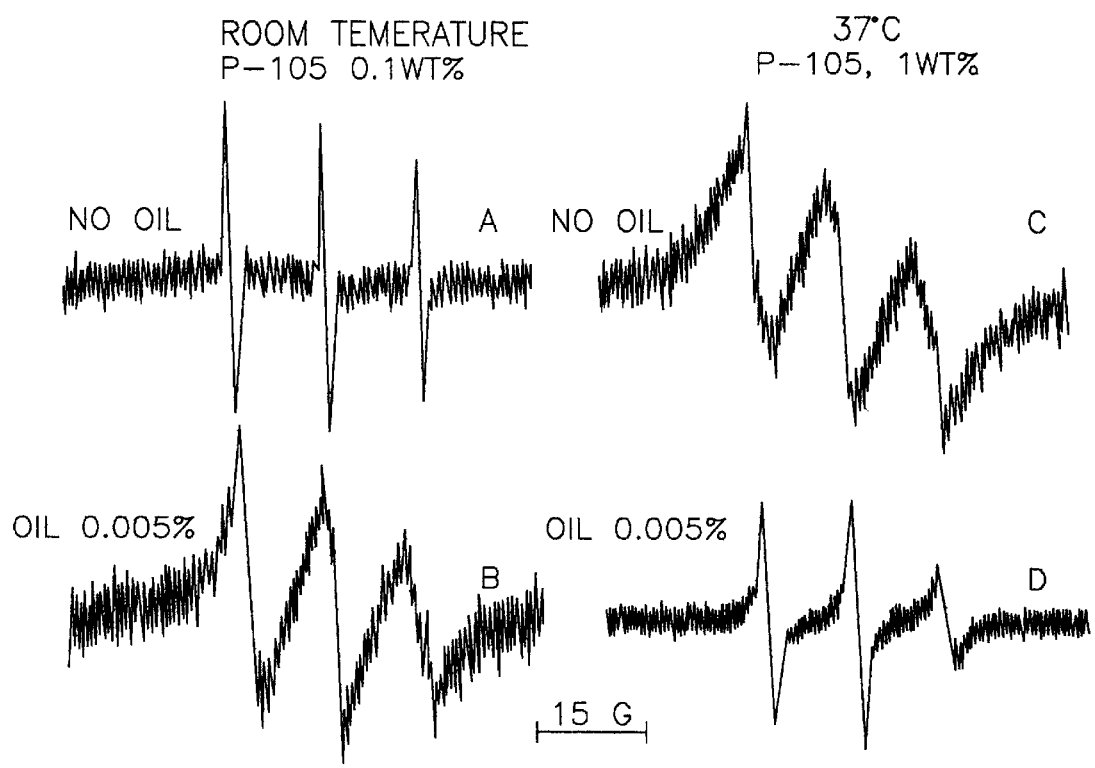
FIG. 5. EPR spectra at room temperature (left) and 37° C. (right) of 16-DS in a 0.1% Plumnic solution (left) or 1% P-triblock solution (right) in the absence (up) or presence (down) of oil; oil concentrations are indicated next to the respective spectrum. The spectra indicate that in the presence of oil in diluted P-triblock solutions, the predominant fraction of the probe (more than 90% for a 0.1% solution) is localized in the hydrophobic environment of P-triblock micelle cores characterized by a~=14.60.

In contrast, when oil-to-P-triblock ratio was low (0.005–0.05% v/v oil in 0.1%–1% P-triblock solutions), oil did not form emulsions but was dissolved in the core of P-triblock micelles, which resulted in micelle stabilization (FIG. 5). In the presence of low concentration of oil, at room temperature, even in 0.01% or 0.1% P-triblock solutions, the predominant fraction of the probe was localized in the hydrophobic environment of P-triblock micelle cores characterized by $a_N$=14.6 G, while in the absence of oil only a negligible concentration of the probe in the hydrophobic environment was found.

The most interesting information provided by the EPR spectra of 16-DS solubilized in diluted P-triblock solutions containing a low concentration of oil is that the structure of these solutions was that of P-triblock micelles rather than oil microemulsions (compare B and D spectra of FIG. 5 with B and C spectra of FIG. 4).

In conclusion, the introduction of low concentrations of vegetable oil stabilized micelles against degradation upon dilution. Introduction of oil did not compromise solubilization efficiency of P-triblock micelles for anticancer drugs.

Figure 6:
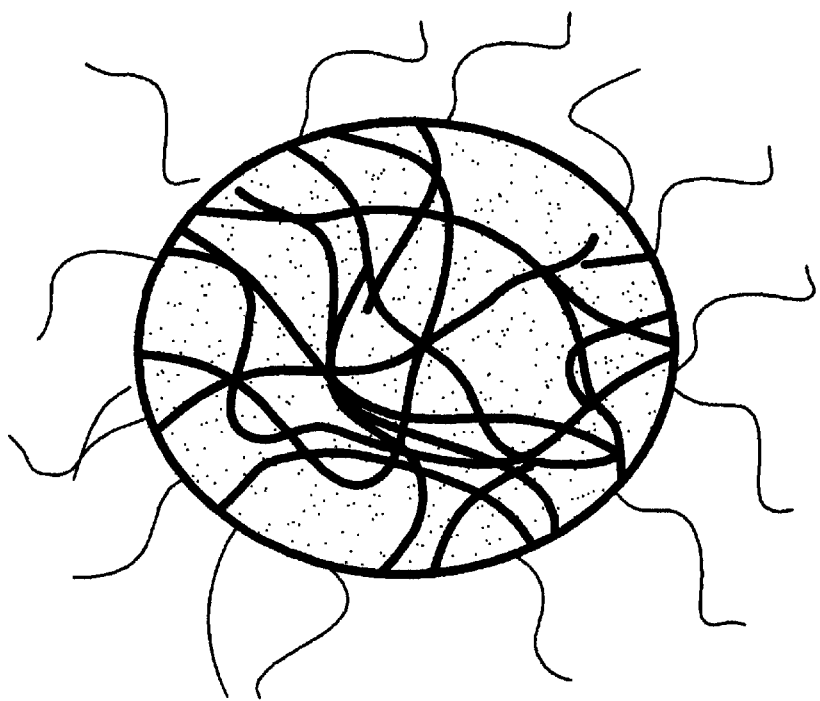
FIG. 6. A schematic diagram showing the interpenetrating network of PPO blocks and hydrogel molecules.
Figure 7:
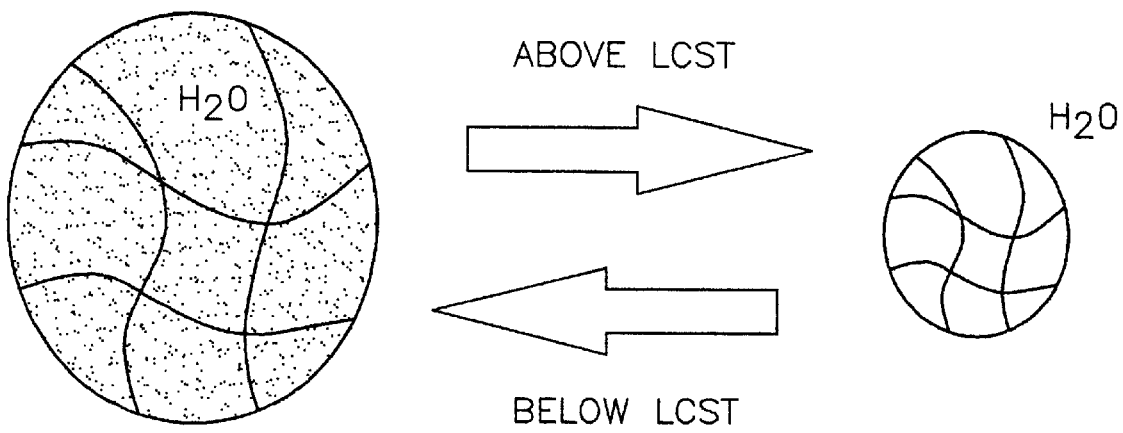
FIG. 7. A schematic diagram showing the reversible collapse and reswelling of a hydrogel stabilized micelle.

Micelle Stabilization by Developing the
Interpenetrating Network of a Polymeric Surfactant
and a Temperature-responsive LCST Hydrogel This experiment shows a novel synthetic pathway to stabilize P-triblock micelles by polymerizing a temperature-responsive low critical solution temperature (LCST) hydrogel in the micelle core. The hydrogel-forming polymer produced the interpenetrating network inside the core of P-triblock micelles. (See FIG. 6) The rational behind this approach was that at room temperature the LCST hydrogel was in a swollen state, which provided for a very high drug loading capacity for lipophilic and hydrophilic drugs. At physiological temperatures, the micelle-encapsulated gel collapsed, "locking" the core of the micelle thus preventing micelles from rapid degradation upon dilution. (See FIG. 7) This new drug delivery system is known under the trademark PLUROGEL, which will be generically referred to herein as P-gel. P-gel is a sterically protected nano-dispersed hydrogel.

Figure 16:
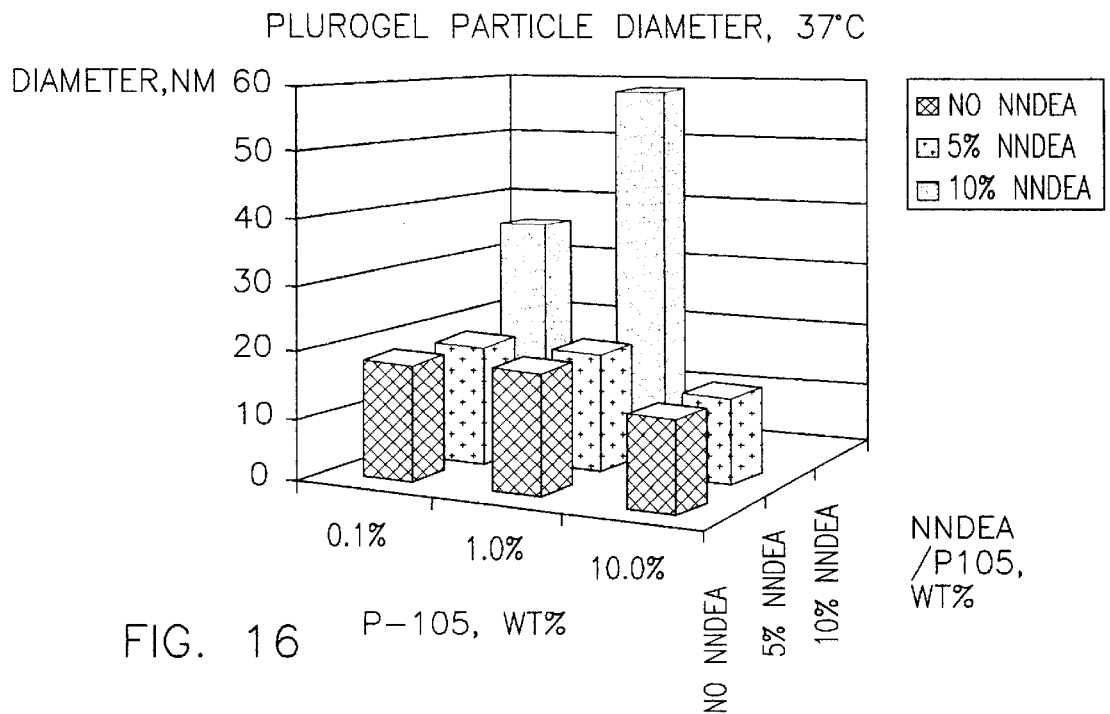
FIG. 16. A graph showing particle sizes of NNDEA stabilized micelles at 37° C.

The sizes of P-gel particles were measured by dynamic light scattering. P-gel particles were larger than P-triblock micelles (particle diameter ranged between 30 nm and 400 nm depending on P-triblock concentration, temperature, and type of a gel-forming monomer. This is to be compared to 12–15 nm for P-triblock micelles at 37° C.). An example of particle sizes for P-gel particles is shown in FIG. 16. P-gel particle size is advantageous for drug delivery applications.

An example of a protocol of P-gel polymerization is given below. N-isopropylacrylamide (NiPAAm) (NI was carried out in inert atmosphere at 70° C. for 24 hours. Upon termination of polymerization, the unreacted monomer, crosslinking agent, and initiator was separated by dialysis through a 1000 D cutoff membrane against PBS.

Obtained P-gel solutions were clear at room temperature. They manifested a sharp, completely reversible transition at 32° C. (e.g. at LCST for a hydrogel), characterized by a formation of a very stable slightly milky dispersion.

When a monomer was polymerized without P-triblock, it precipitated from a reaction medium at any temperature.

When polymerized without neither P-triblock nor a crosslinker, the polymer precipitated from a reaction medium, but could be solubilized by addition of P-triblock, with a formation of a milky dispersion.

In another example, N,N-Diethylacrylamide (NNDEA) was polymerized in the presence of P-triblock P-105 micelles. The polymerizations resulted in an interpenetrating network of NNDEA and P-105 that stabilizes the micelles at concentrations below the critical micellar concentration of free P-105. The NNDEA was crosslinked with N,N'-Bis (acryoyl)cystamine (BAC) and the degree of micellar stability was determined using dynamic light scattering and the fluorescent probe diphenylhexatriene (DPH). The increased micellar stability was not permanent and disappeared over a time period of days to weeks.

40 ml of double distilled water containing 10 wt % P-triblock P-105 was added to a round bottom flask. N,N-diethylacrylamide (NNDEA) monomer was added to give concentrations ranging from 0 to 1 wt % monomer. BAC was added as a crosslinking agent to give BAC:NNDEA mole ratios ranging from zero to 1:20. AIBN was added as an initiator and the flask was connected to a water condenser and purged with nitrogen for at least one hour. The system was then allowed to polymerize for 24 hours at 65° C. with magnetic stirring and a continuous nitrogen purge.

Molecular Weight Determination

The molecular weight of un-crosslinked p(NNDEA) was investigated by gel permeation chromatography using a Waters GPC system (Milford, Mass.) (model 515 pump with styragel columns and a model 2410 refractive index detector). Polymerization samples were dried, dissolved in tetrahydrofuran, and filtered through a 0.22 $\mu$m teflon filter before being injected into the GPC system. Molecular weights were determined using polystyrene standards and Water's Millennium$^{32}$ software.

Figure 12:
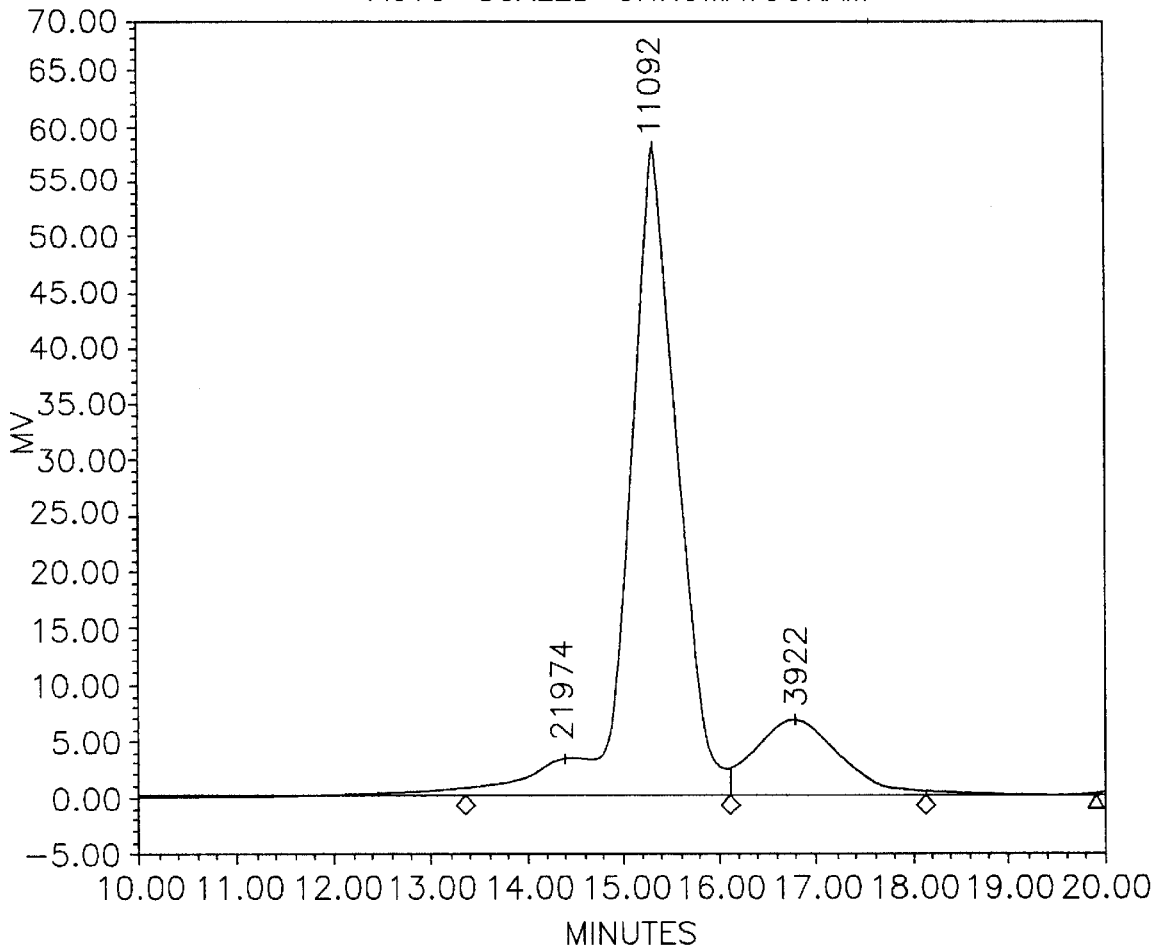
FIG. 12. Is a chromatogram showing the molecular weight of a NNDEA P-gel.

Molecular weight for NNDEA P-gel was found to be 21,974. (See FIG. 12).

NNDEA P-Gel Particle Stabilization and Microenvironment

Figure 13:
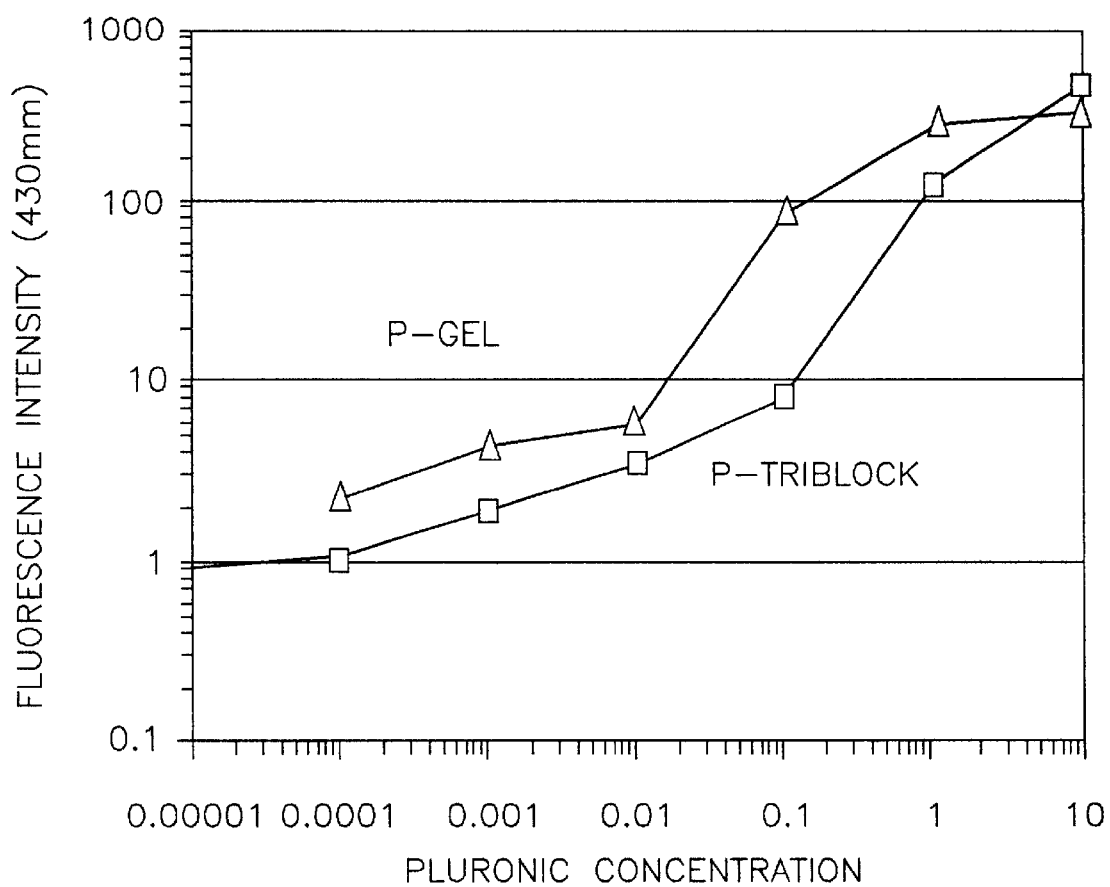
FIG. 13 Is graph showing preservation of hydrophobic cores of micelles at very high dilutions of P-gel samples.

The critical micellar concentration (CMC) and micellar stability were studied for NNDEA p-gel using a fluorometer with DPH as a fluorescent probe. The emission spectra of DPH is highly dependent upon the hydrophobicity of the local environment and is therefore useful for determining the presence of a hydrophobic environment. Samples were serially diluted in double distilled water to give P-triblock P-105 concentrations ranging from 10 wt % to 0.0001 wt %. DPH was added to give a final DPH concentration of 0.1 $\mu$g/ml. The samples were excited at 360 nm and the emission at 430 nm was measured. The temperature was controlled with a re-circulating thermostatic bath connected to the cuvette holder. The results show the noticeable preservation of hydrophobic cores at very high dilutions of P-gel samples. (FIG. 13)

Turbidity Measurements

Figure 15:
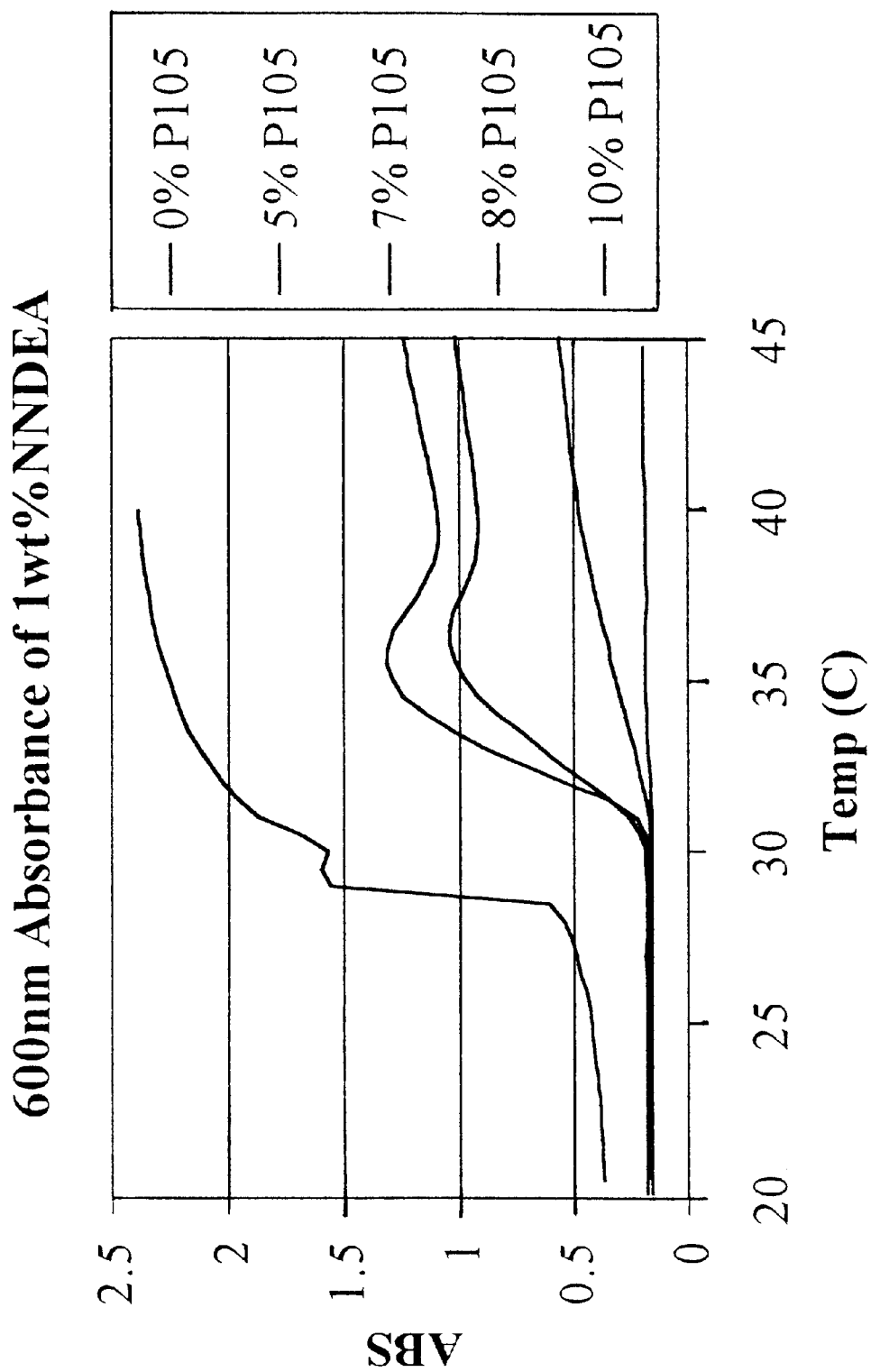
FIG. 15. A graph showing polymerized NNDEA light scattering.

The collapse of p(NNDEA) into a hydrophobic state at its LCST is visible as an increase in the turbidity of an aqueous solution as the resulting particulates scatter visible light. P-triblock P-105 micelles have diameters much smaller than the wavelength of visible light; and therefore do not increase the turbidity of the solution. The absorbance of 600 nm light was used as a means of determining whether or not the p(NNDEA) had aggregated into particles large enough to scatter light. FIG. 15 shows that as NNDEA is polymerized in the presence of increasing concentrations of P-triblock P-105 the increase in turbidity as the temperature is raised past the LCST begins to disappear. At a concentration of 10 wt % P-triblock P-105 and 1 wt % NNDEA there is almost no increase in the turbidity upon heating. It is believed that at these concentrations most of the NNDEA has polymerized totally within the micellar cores and does not aggregate with other particles upon thermally induced collapse.

Phase State of P-gel Nanoparticles

To characterize phase state of P-gel nanoparticles at various temperatures, the EPR and fluorescence techniques were used with 16-DS as a spin probe and DPH as a fluorescent probe, respectively. The probe was solubilized in the initial P-gel solution (10% P-triblock/1% poly (NiPAAm)) or 10% P-triblock/1% poly (NNDEA) at room temperature.

The results of this study are summarized below.

NiPAAm P-gel

Figure 8:
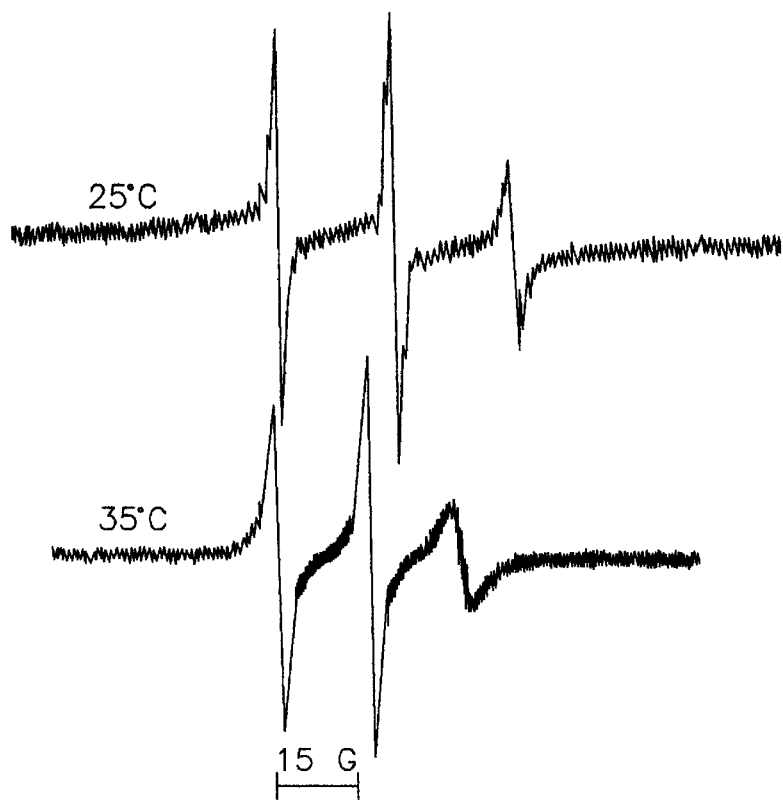
FIG. 8. The EPR spectra of 16-DS solubilized in 10% P-105/1% poly(NiPAAm) nanoparticles. At room temperature (upper spectrum), the probe is localized predominantly in the hydrophilic environment of a swollen hydrogel; heating the P-gel solution to 37° C. (above hydrogel's LCST) results in probe re-distribution: 94% of the probe is transferred into the hydrophobic environment (lower spectrum).

Effect of temperature. The presence of a swollen poly (NiPAAm) gel in a 10% P-triblock solution hampered the formation of P-triblock micelles at room temperature. For a 10% P-triblock solution without a gel, the probe was localized exclusively in the hydrophobic environment of P-triblock micelles characterized by a hyperfine splitting constant $a_N$=14.6 G and a rotational correlation time, $t_{rot}$=1.165 ns (see Table 2 and FIG. 3, upper spectrum). In contrast, in a 10% P-triblock/1% poly(NiPAAm) P-gel solution, the probe partitioned hydrophobic and hydrophilic microphases, with a predominant (more than 90%) localization in the hydrophilic environment ($a_N$=15.5 G) (FIG. 8, upper spectrum). Probe motion in the hydrophilic phase of a P-gel was much more restricted than in the aqueous phase outside P-triblock micelles ($t_{rot}$=0.49 ns in a P-gel vs. trot<0.1 ns in a hydrophilic phase of diluted P-triblock solutions). This implies that at room temperature, in a P-gel, the probe was located predominantly in the swollen hydrogel microphase.

Heating a 10% P-triblock/1% poly(NiPAAm) P-gel solution to 37° C. (i.e. above the LCST of the hydrogel, which is 32° C.) resulted in probe re-distribution. The predominant fraction of the probe (94%/o) was located in the hydrophobic environment ($a_N$=14.6 0, $t_{rot}$=0.59 ns) (FIG. 8, lower spectrum). The EPR parameters of this phase were equal to those for P-triblock micelles (Table 2). About 6% of the probe remained in the hydrophilic phase, which was characterized by lower microviscosity than at room temperature.

The hydrophobic environment of the probe was presumably that of the core of P-gel nanoparticles that comprised P-triblock micelles interpenetrated by the network of a collapsed hydrogel.

Above the LCST of the hydrogel, P-gel formed stable dispersions that did not precipitate; this implies that P-gel nanoparticles were stabilized by PEO chains on their surfaces.

It appears important for the drug delivery applications that a small fraction of the probe (6%) was expelled from the core of the particles when the gel collapsed. It implies that for a lipophilic drug, a small fraction of the drug could be released into the environment upon the collapse of the gel; this fraction of the drug will be taken up by the cells via regular mechanisms typical of a particular drug/cell system. This may provide for a precise external control of drug delivery. For instance, the transition temperature of a gel may be set slightly above the physiological temperature; the repeated heating/cooling cycles of the tumor volume (e.g. by pulsed ultrasound) would result in a controlled drug release from nanoparticles.

Effect of a P-gel dilution. At room temperature, dilution of the initial 10% P-triblock/1% poly(NiPAAm) P-gel solution resulted in a drop of microviscosity of the hydrophilic phase; a rotational correlation time for the probe in the hydrophilic phase decreased from 0.48 ns to 0.10 ns upon a 10-fold dilution, For a 100-fold diluted P-gel solution, probe motion in the hydrophilic phase was even faster ($t_{rot}$=0.08 ns) indicating progressive hydration of a gel phase. No hydrophobic phase was observed in diluted P-gel solutions at room temperature.

Figure 9:
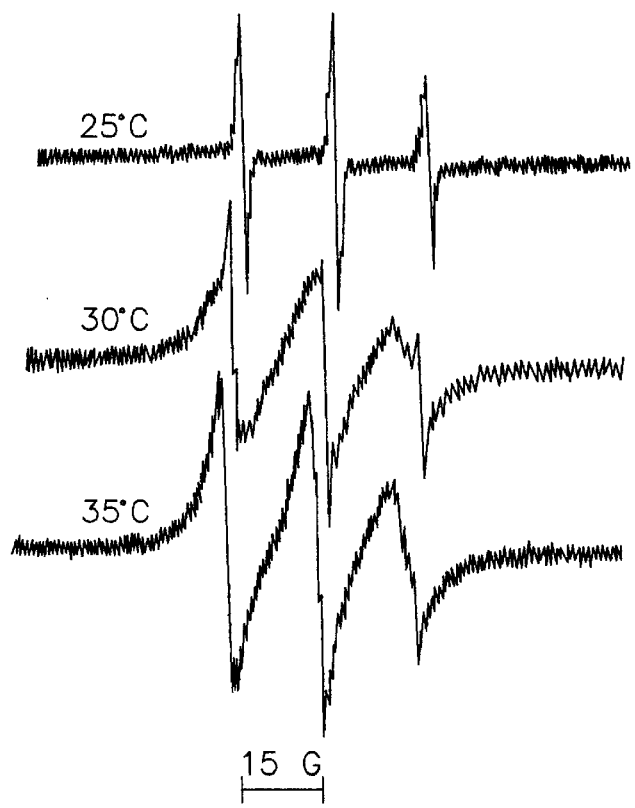
FIG. 9. The EPR spectra of 16-DS in a 10-fold diluted initial P-gel solution (final concentration 1% P-triblock/ 0.1% poly(N1PAAm). In a diluted solution, the hydrogel phase has much lower microviscosity than in the initial P-gel solution (compare upper spectrum of this Figure to that of FIG. 8). Spectral changes with increasing temperature indicate progressive micellization of a diluted P-gel solution.

Upon heating above the LCST of the hydrogel, a hydrophobic phase appeared in diluted P-gel solutions, and a temperature-dependent equilibrium was established between hydrophobic and hydrophilic microphases. This is clearly manifested in FIG. 9 for a 1% P-105/0.1% poly (NiPAAm) P-gel solution. The fraction of the probe in the hydrophobic phase increased dramatically with increasing temperature indicating progressive formation of the particles with hydrophobic cores. When compared to control P-triblock solutions of equal concentrations (without a gel), the fraction of the probe in the hydrophobic phase was always higher in a P-gel than in P-triblock. According to the results of spectra simulation, at 37° C., in a 100-fold diluted initial P-gel solution (final concentration 0.1% P-triblock/ 0.01% poly(NiPAAm), 86% of the probe was still retained in the hydrophobic phase of the P-gel, whereas in non-stabilized P-triblock solutions of the same concentration, the probe was localized predominantly in the hydrophilic environment. Even upon 1000-fold dilution of the initial P-gel solution, about 33% of the probe remained in the hydrophobic environment, indicating the preservation of hydrophobic cores of nanoparticles; no micelles were preserved in non-stabilized P-triblock solutions of equal concentration (Table 2,).

TABLE 2

Rotational correlation time $t_{corr}$, hyperfine splitting constant $a_N$ and a fraction of a probe in the hydrophobic environment for a 16-DS spin probe.

| Sample | T° C. | $t_{corr}$(ns)/$a_N$(G) hydrophobic | $t_{corr}$(ns)/$a_N$(G) hydrophobic | % hydrophobic |
|---|---|---|---|---|
| P-105 10% | RT | 1.17/14.6 | — | 100% |
| P-gel 10%* | RT | — | 0.48/15.5 | <10% |
| P-gel 1% | RT | — | 0.10/15.9 | 0% |
| P-gel 0.1% | RT | — | 0.08/15.9 | 0% |
| P-105 10% | 37° C. | 0.59/14.6 | — | 100% |
| P-105, 0.1% | 37° C. | 0.60/14.7 | — | 54% |
| P-105 0.01% | 37° C. | — | <0.1/15.6 | 0% |
| P-gel 10% | 37° C. | 0.59/14.6 | — | 94% |
| P-gel 1% | 37° C. | — | — | 99% |
| P-gel 0.1% | 37° C. | 0.80/14.5 | — | 86% |
| P-gel 0.01% | 37° C. | — | — | 33% |

*Percentage indicates P-triblock weight concentration. A concentration of a gel-forming polymer is 10-fold lower.

It is noteworthy that for the same P-triblock concentration, the properties of the hydrophobic phase in a P-gel differed from those in P-triblock: the environment of the probe was more hydrophobic and the motion of the probe was more restricted in a P-gel (see Table 2.).

These data indicate that the collapse of the hydrogel upon heating a P-gel above gel's LCST results in tighter packing of molecules and lower degree of hydration of the cores of P-gel nanoparticles when compared to those in P-triblock micelles.

In conclusion, developing the interpenetrating network of the LCST hydrogel in the core of P-triblock micelles stabilizes hydrophobic cores of P-gel nanoparticles. Drug loading experiments showed that drug loading capacity of P-gel nanoparticles was higher than that of P-triblock micelles.

P-gel particles are expected to have a long circulation time in blood since they have protective poly(ethylene oxide) chains on their surface.

The properties of P-gel nanoparticles described above make them excellent prospects as carriers of lipophilic drugs.

Drug Distribution and Release from P-triblock Micelles

Figure 14:
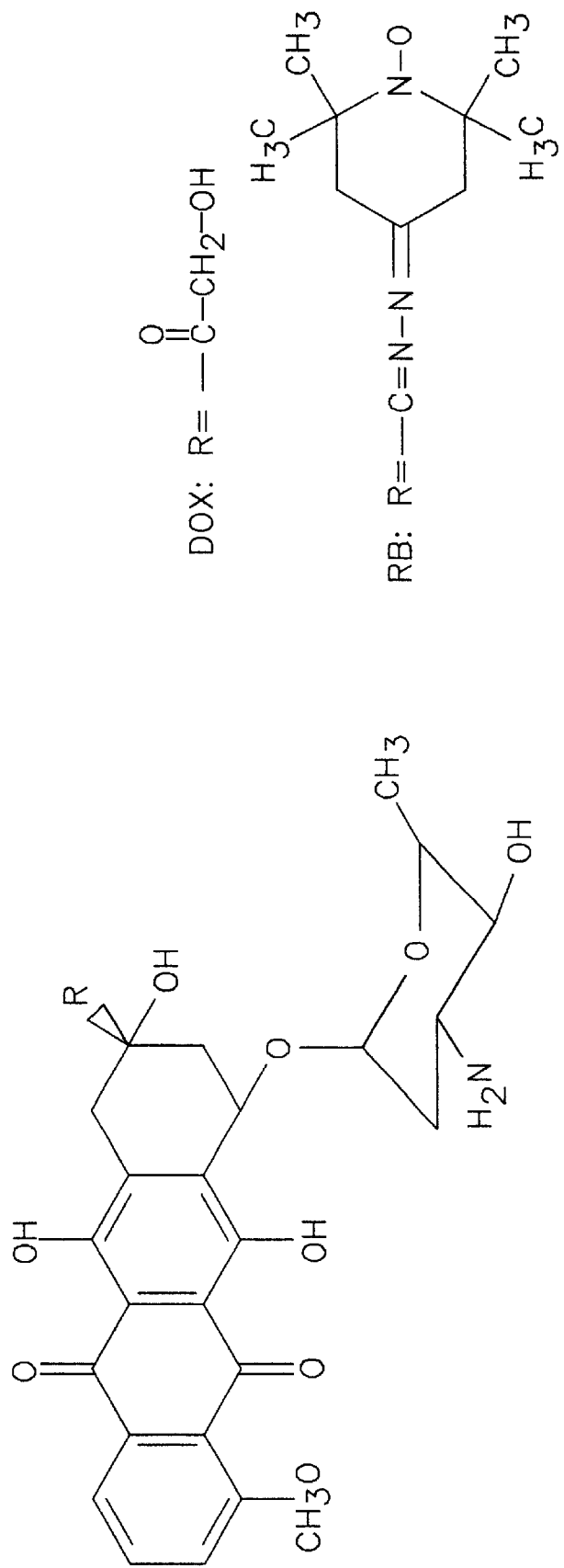
FIG. 14. A scheme showing conjugation of nitroxide radical (1-oxo-2,2,6,6-piperidone-4-hydrazone) to DOX molecule to form Rb.

Two DNA intercalating anti-cancer drugs, DOX and Rb were used in this study. DOX is widely used in clinical practice as a chemotherapeutic agent. However, like other anti-cancer drugs of anthracyclin family, DOX is cardiotoxic due to the induced production of active oxygen radicals [38, 39]. To reduce a cardiotoxicity, a paramagnetic Tempo-type nitroxide radical (1-oxo-2,2,6,6-piperidone-4-hydrazone) was conjugated to DOX molecule to form Rb (FIG. 14) [40]. The nitroxide moiety in position 14 served as a radical trap. A unique Rb molecule is both fluorescent and paramagnetic, which allows fluorescence and EPR spectroscopy to be used independently in investigations of drug uptake, distribution and metabolism. This makes Rb a powerful research tool.

Rb was used as a spin- and fluorescent probe to monitor drug distribution in P-triblock micelles and P-gel nanoparticles.

Drug Localization in P-triblock Micelles in the Absence of a Hydrogel

Figure 10:
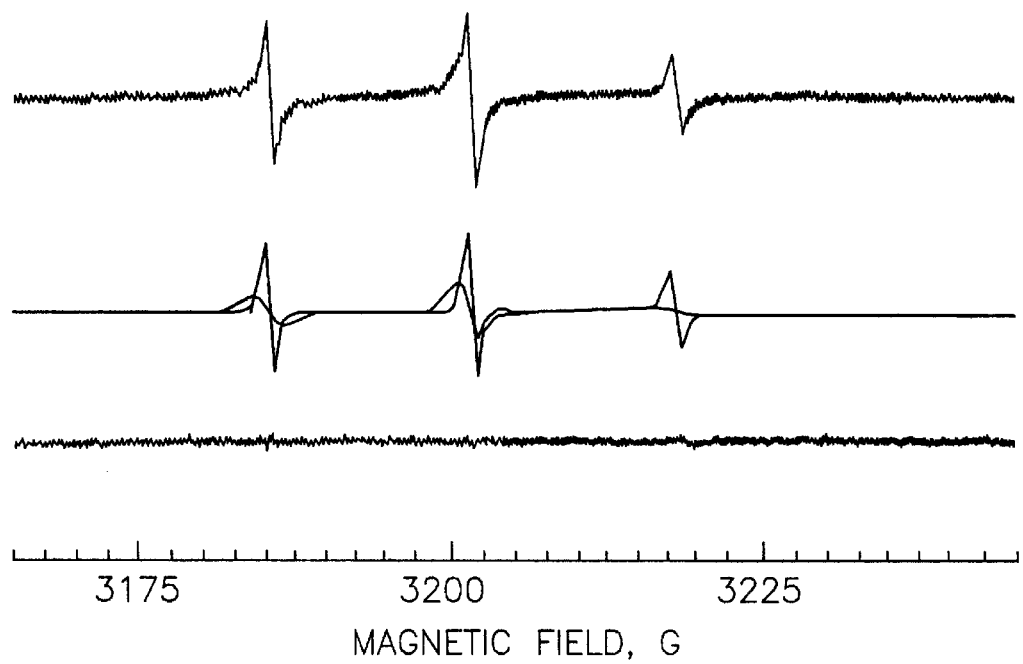
FIG. 10. The EPR spectrum at room temperature of Rb (0.1 mM) solubilized in 10% P-triblock solution showing the superposition of signals arising from two drug populations differing in motion intensity. Upper spectrum— experiment; middle—simulation using the ENVoigt program; lower—differential spectrum between the experimental and simulated spectra. Both signals correspond to the probe located in the hydrophilic-environment; sharp spectrum corresponds to a probe with faster motion.

At room temperature, in 10% P-triblock PLURONIC P-105 solutions, EPR spectra revealed two populations of Rb molecules characterized by $n_A$=16.3 G and $n_A$=16.1 G respectively, with a molar ratio of 1:2.5 (FIG. 10). EPR signals produced by both Rb populations corresponded to molecules located in the hydrophilic environment, one being slightly more hydrophilic than the other (for Rb in PBS, the hyperfine splitting constant $n_A$=16.4 G). The population of the probe in a more hydrophilic environment ($n_A$=16.3 G) was highly mobile ($t_{rot}$=0.11 ns) and was presumably localized close to the corona/aqueous interface of P-triblock micelles. The second drug population ($n_A$=16.1 G) was characterized by a much more restricted dynamics ($t_{rot}$=1.35 ns) and was presumably localized at the interface between the core and corona of P-triblock micelles. This conclusion follows from comparison of the results of EPR and fluorescence experiments as explained below.

Figure 23:
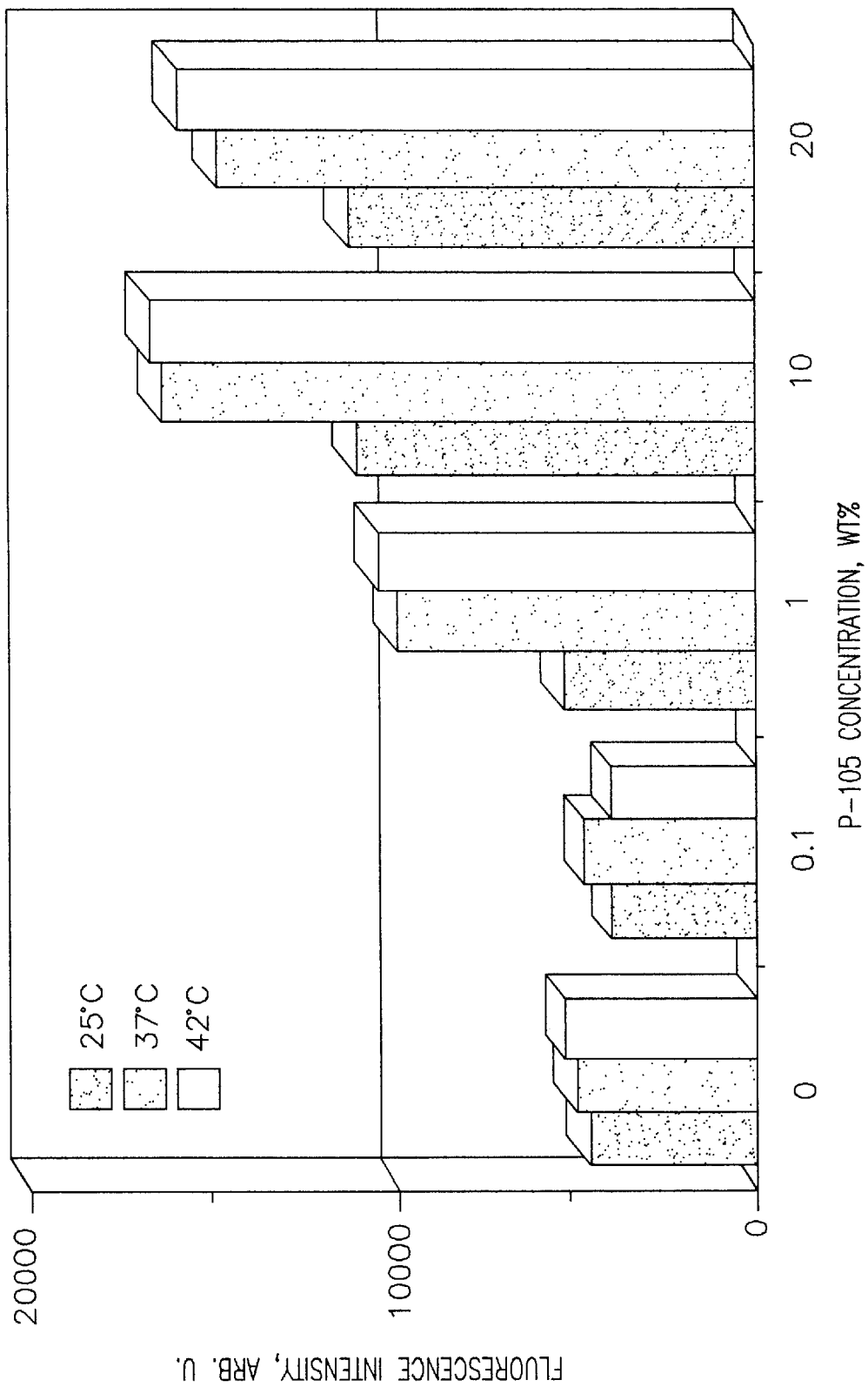
FIG. 23. Effect of temperature on Rb. fluorescence intensity in PBS and P-triblock PLURONIC P-105 solutions. [Rb]=10 μg/ml.

The anthraquinone part of Rb molecule is inherently fluorescent. Rb fluorescence is quenched in collisions with water molecules; when Rb molecules are screened from collisions with water, theft fluorescence increases manifold. This phenomenon was used to study P-triblock P-105 micellization [31]: As illustrated in FIG. 23, Rb fluorescence increased sharply upon the onset of micelle formation in P-triblock solutions; as could be expected (see, e.g.[22]), P-triblock concentration corresponding to the onset of micelle formation decreased with increasing temperature.

Information produced by the fluorescent part of Rb molecule implied that at room temperature and in 10% P-triblock solutions, about 70% of Rb molecules were localized in the hydrophobic environment of micelle cores; this is in contradiction to the information given by the paramagnetic (nitroxide) part of Rb molecule which implied that the drug was localized in the hydrophilic environment of micelle corona.

A feasible explanation of this discrepancy is that Rb molecules were localized at the interface between the PPO core and PEO corona of P-triblock micelles, hydrophobic anthraquinone part being inserted into the micelle core while more polar nitroxide part looking into the corona; this also indicated that in P-triblock micelles, the transition from core to corona was rather sharp (within several angstroms).

Drug Localization in P-gel-nanoparticles at Room Temperature

For a 10% P-triblock/1% poly(NiPAAm) P-gel solution, similar to a 10% P-triblock solutions without a hydrogel, the EPR spectra revealed two populations of Rb molecules in the hydrophilic environment characterized by the same hyperfine splitting parameters; a fraction of rotationally restricted molecules was slightly higher in P-gel nanoparticles indicating that a larger fraction of drug molecules was drawn into the depth of the nanoparticles (78% vs. 71%).

Effect of Temperature on Drug Localization in P-gel-nanoparticles

Heating a P-gel to 37° C., e.g. above gel's LCST, resulted in the changes of the EPR parameters of Rb molecules; again, two populations of the drug molecules were revealed, one being characterized by $n_A$=16.3 G (close to that at room temperature), and the other by $n_A$=15.7 G. The second hyperfine splitting constant was significantly lower than $n_A$=16.1 G measured at room temperature; this splitting constant was close to $n_A$=15.40 measured for Rb molecules localized in the bilayers of DMPC liposomes. This finding implied that heating the P-gel above gel's LCST resulted in drug transfer into a more hydrophobic environment, presumably that of hydrophobic cores of P-gel nanoparticle. The overall fraction of the drug in the cores of P-gel nanoparticle was 73%. These data are in agreement with those provided by the 16-DS spin probe.

Effect of Dilution on Drug Distribution in a P-gel

Figure 11:
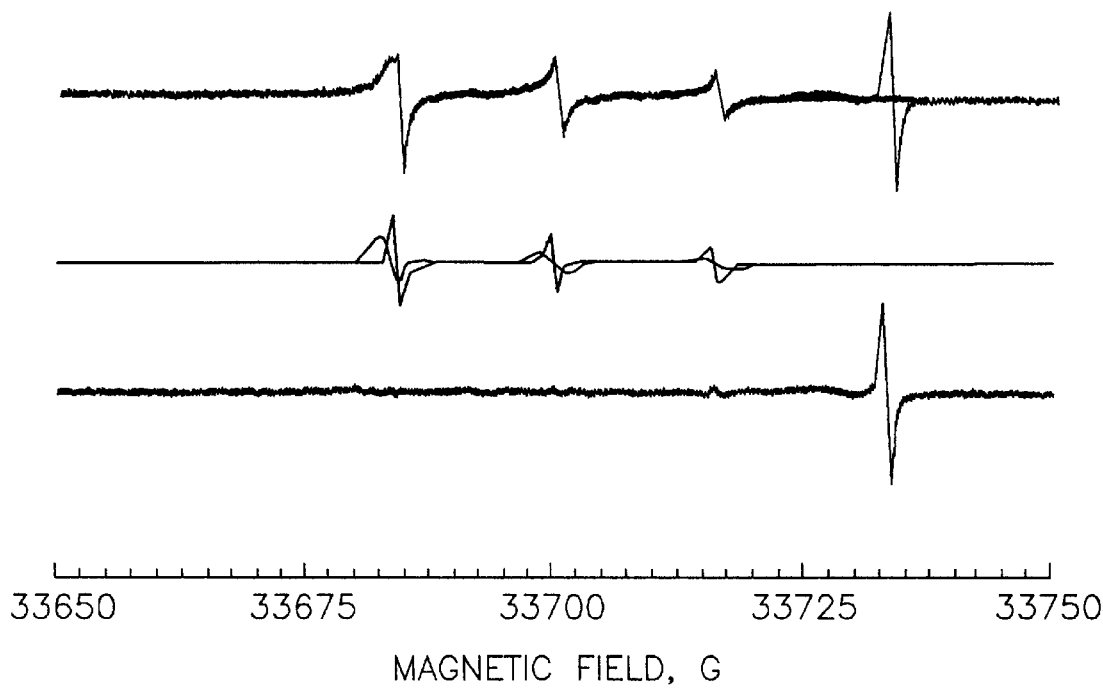
FIG. 11. W-band EPR spectrum at room temperature of a 100-fold diluted initial P-gel solution manifesting probe transition from the hydrophilic to the hydrophobic environment upon dilution, upper spectrum—experiment; middle— simulation; lower spectrum—differential spectrum between the experimental and simulated spectrum (a sharp right line is a $Ms^{2-}$ standard).

Upon a 100-fold dilution of the initial 10% P-triblock/1% poly(NiPAAm) P-gel solution at room temperature, Rb was transferred from the aqueous phase into a less hydrated one, as indicated by splitting of the low-filed line in the high-frequency EPR spectra (FIG. 11). This is a somewhat unexpected observation because drug partitioning considerations would lead to the opposite prediction. However, three types of water molecules should be considered for a P-gel: a free water, water in hydrogel pores, and water associated with PEO corona of nanoparticles. The degree of hydration of a hydrogel phase increases upon dilution; since Rb has a low aqueous solubility, it is drawn deeper into the less hydrated environment. A similar effect is observed for a 16-DS probe.

An advantage is that the p-gel micelles are stable for drug delivery, but not so stable that they cannot be degraded by the body. After a matter of weeks, the stabilized p-gels will gradually destabilize. This allows sufficient time to function effectively as a drug delivery system, but the degradation will allow eventual removal from the body. This is unlike many drug delivery systems that involve stable components that are slow to be removed from the body. The thermodynamics of the p-gel system direct the system toward dissolution, and instability, but the kinetics are very slow.

Effect of Micelle Structure on the Intracellular Drug Uptake

In this study, HL-60 cells were incubated at 37° C. with DOX or Rb. The drugs were either dissolved in the RPMI medium (or PBS), or they were solubilized in P-triblock PLURONIC P105 solutions of various concentrations.

The uptake of either drug was somewhat enhanced at P-triblock concentration of 0.1%, which is below the CMC for the formation of micelles with hydrophobic cores. This is in agreement with Kabanov's data [33] and implies that P-triblock molecules in a unimeric form or in loose aggregates enhance the permeability of cell membranes toward the drugs (FIG. 17) [31].

Figure 17:
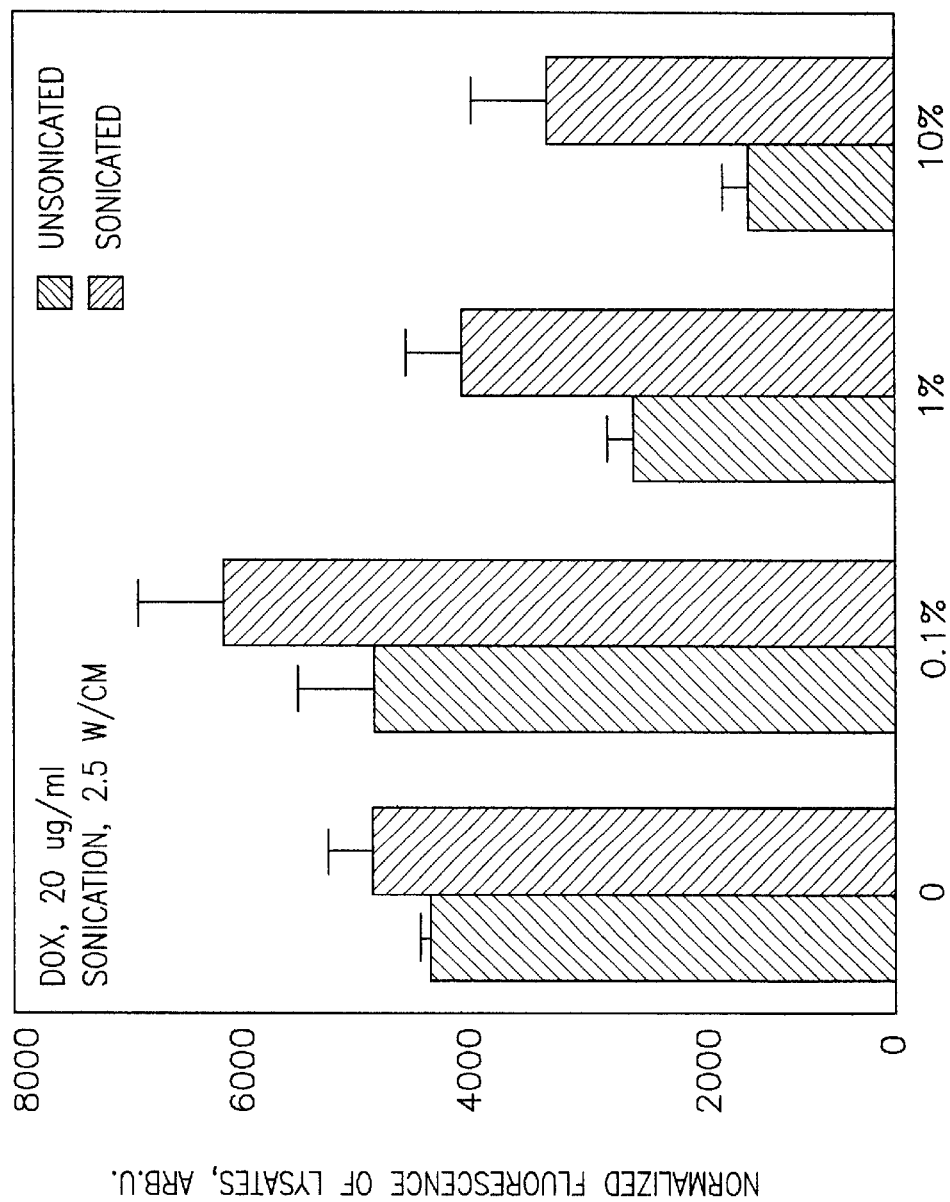
FIG. 17. Effect of sonication on the intracellular uptake of DOX by HL-60 cells: fluorescence of HL-60 cell lysates, normalized to the cell concentration, as a function of P-triblock PLURONIC P-105 concentration; ([DOX]=3.4 μg/ml, incubation/sonication time 1 h).

Drug sequestering in P-triblock PLURONIC P-105 micelles with hydrophobic cores caused substantial decrease in drug uptake by HL-60 cells, indicating that dense micelles inhibited drug interaction with the cells (FIG. 17).

Acoustically Activated Drug Release from Unstabilized and Stabilized P-triblock Micelles Under Continuous Wave Ultrasound For these experiments, a home-made real-time fluorescence detection chamber was used. (FIG. 18) The apparatus employed a single-line argon-ion laser (Ion Laser Technology, Model 5500 A) whose beam was divided by a variable beam splitter (a graded metal-film neutral density, filter). One portion of the beam was sent directly to a silicon photodetector (Newport Model 818-SL with 835 display) to monitor the laser power. The other portion was directed into the glass cuvette containing the trial solution to be sonicated. It was designed in collaboration with Dr. Christensen (University of Utah); details of the design will be described elsewhere.

The effect of ultrasound on drug release from micelles was measured based on differences in fluorescence intensity of Rb or DOX within and outside micelles. A constant wave and pulsed ultrasound was applied to drug solutions at 37° C. With no P-triblock present, insonation had no effect on drug's fluorescence.

When Rb or DOX were solubilized in 10% P-triblock solution (micelles with hydrophobic cores), insonation caused decrease in drug fluorescence intensity.

Upon the termination of insonation, the fluorescence intensity recovered to its original level. The effect was highly reproducible in all experiments. The drop in fluorescence indicated that a portion of Rb or DOX was expelled from micelles under sonication. The onset of a steady fluorescence intensity level under sonication resulted from the equilibrium between drug release and re-encapsulation.

Acoustically activated drug release was observed also for hydrogel-stabilized micelles. The reencapsulation proceeds very fast. These findings are important for the drug delivery application of acoustically-activated micelles. In conclusion, ultrasound induced release of some fraction of the encapsulated drug from micelles; drug was re-encapsulated when ultrasound was switched off.

Acoustical Triggered Release of Drugs from Polymeric Micelles Under Pulsed Ultrasound In clinical situation pulsed ultrasound appears to be superior to CW since pulse, and pulse duration and sequence can be carefully controlled. Also, heating and burning of skin can be prevented by the application of pulsed ultrasound with appropriate pulse sequences.

A custom ultrasonic exposure chamber with real-time fluorescence detection was used to measure acoustically-triggered drug release from P-triblock PLURONIC P-105 micelles under continuous wave (CW) or pulsed ultrasound in the frequency range of 20 kHz to 90 kHz. The measurements were based on the decrease in fluorescence intensity when drug was transferred from the micelle core to the aqueous environment. Two fluorescent drugs were used: doxorubicin (DOX) and its paramagnetic analogue, ruboxyl (Rb). P-triblock PLURONIC P-105 at various concentrations in aqueous solutions was used as a micelle-forming polymer. Drug release was highest at 20 kHz ultrasound and dropped with increasing ultrasonic frequency despite much higher power densities. These data suggest an important role of transient cavitation in drug release. The release of DOX was higher than that of Rb due to stronger interaction and deeper insertion of Rb into the core of the micelles. Drug release was higher at lower P-triblock concentrations, which presumably results from higher local drug concentrations in the core of P-triblock micelles when the number of micelles is low. At constant frequency, drug release increased with increasing power density. At constant power density and for pulse duration longer than 0.1 s, peak release under pulsed ultrasound was the same as stationary release under CW ultrasound. Released drug was quickly re-encapsulated between the pulses of ultrasound, which suggests that upon leaving the sonicated volume, the non-extravasated and non-internalized drug would circulate in the encapsulated form, thus preventing unwanted drug interactions with normal tissues.

Measuring Ultrasound-triggered Real-time Release of DOX and Rb from P-triblock P-105 Micelles The anthraquinone parts of Rb and DOX molecules are inherently fluorescent when excited at a wavelength of 488 nm, making them effective as fluorescent probes. However, Rb and DOX fluorescence is quenched by collisions with water molecules (dynamic quenching). Thus, when Rb and DOX molecules are prevented from collisions with water, for instance by their encapsulation in the hydrophobic core of micelles, their fluorescence increases two- to three-fold [72]. This feature was used in this study to measure drug release from micelles under the action of ultrasound.

Figure 18:
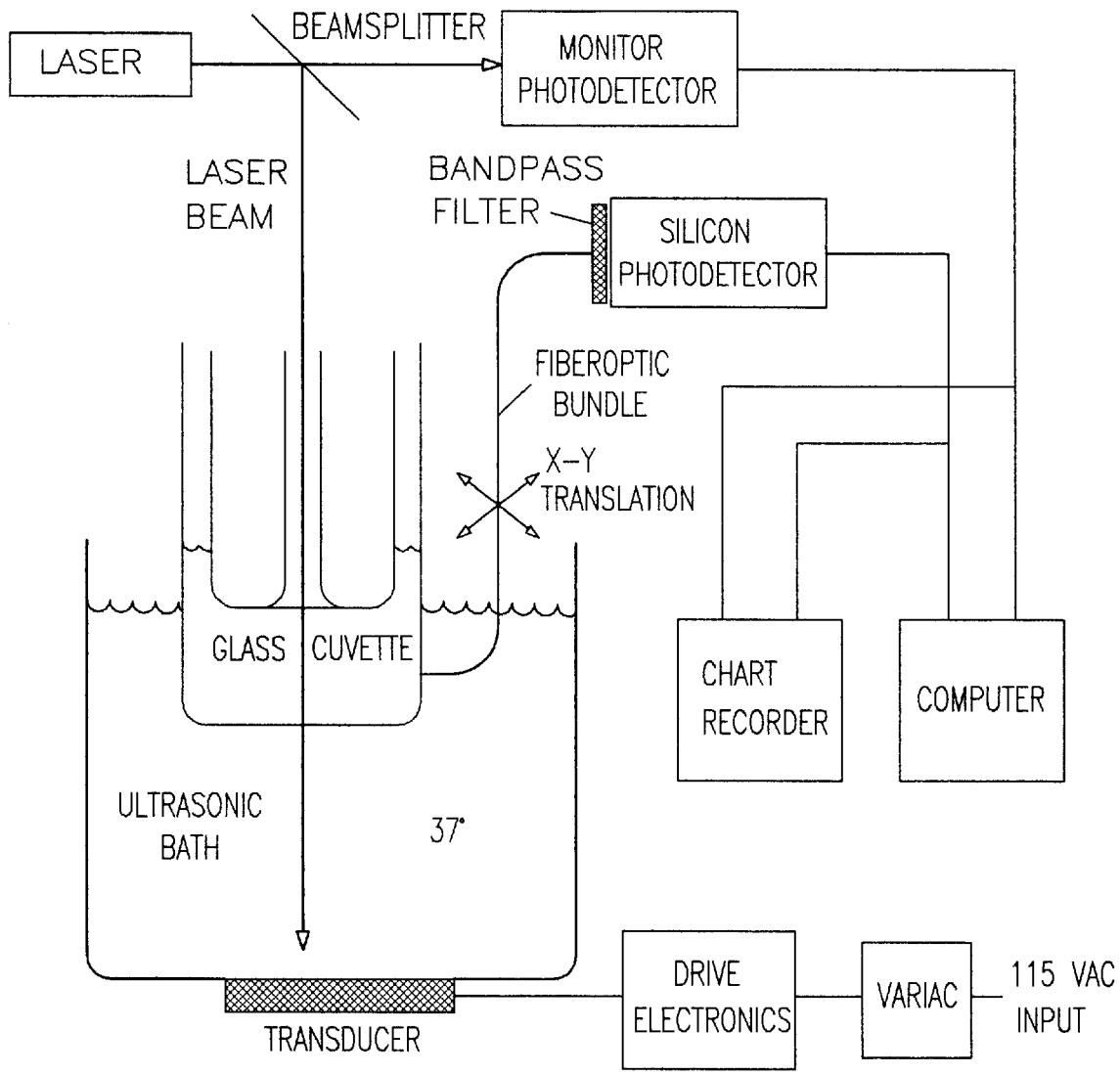
FIG. 18. Experimental arrangement for fiberoptic detection of fluorescence of drug under ultrasound exposure. For 20 kHz exposure, the transducer was controlled by different electronics and was inserted into the exposure bath from above.

Real-time measurements of drug release were performed using a specially designed ultrasonic exposure chamber with fluorescence detection, shown schematically in FIG. 18.

Fluorescence of the drug was excited at an excitation wavelength of 488 nm with an optical power of approximately 0.5 mW in a 2 mm diameter beam. At this light intensity no photobleaching was observed, based on the constant level of drug fluorescence during continuing irradiation for 8 hours. The drug release was quantified by measuring the changes in fluorescence emissions before, during, and after the ultrasound exposure. A fiberoptic probe (a sheathed bundle of multimode glass fibers, 3 mm entrance diameter, 0.6 numerical aperture, and 90 cm in length) was used to collect the fluorescence emission. The light passed through a dielectric bandpass filter with a 35 nm bandwidth centered at 535 nm (Omega Optical Model 535DF35) to a sensitive silicon detector (EG&G Model 450-1). The filter effectively cuts off emissions below 500 nm, including any Rayleigh-scattered laser light. The detector signal was digitized using a 12-bit A/D converter (National Instruments) and sent, along with the digitized monitor photodetector signal, to a Macintosh computer for storage and processing. The analog outputs of both photodetectors were also plotted on a stripchart recorder. The temperature of the ultrasonic exposure chamber was maintained at 37° C. by circulating thermostated water throughout the sonicating bath.

The glass cuvette used to measure drug release had two open tubes for filling or removing drug solution and one sealed tube in the middle to allow the excitation beam to enter the solution through a flat stationary surface. This prevents any distortions that could otherwise arise from waves on the surface of the sonicated liquid. The main chamber of the cuvette was completely filled with the solution, and the excess liquid partially filled the side tubes.

Figure 19:
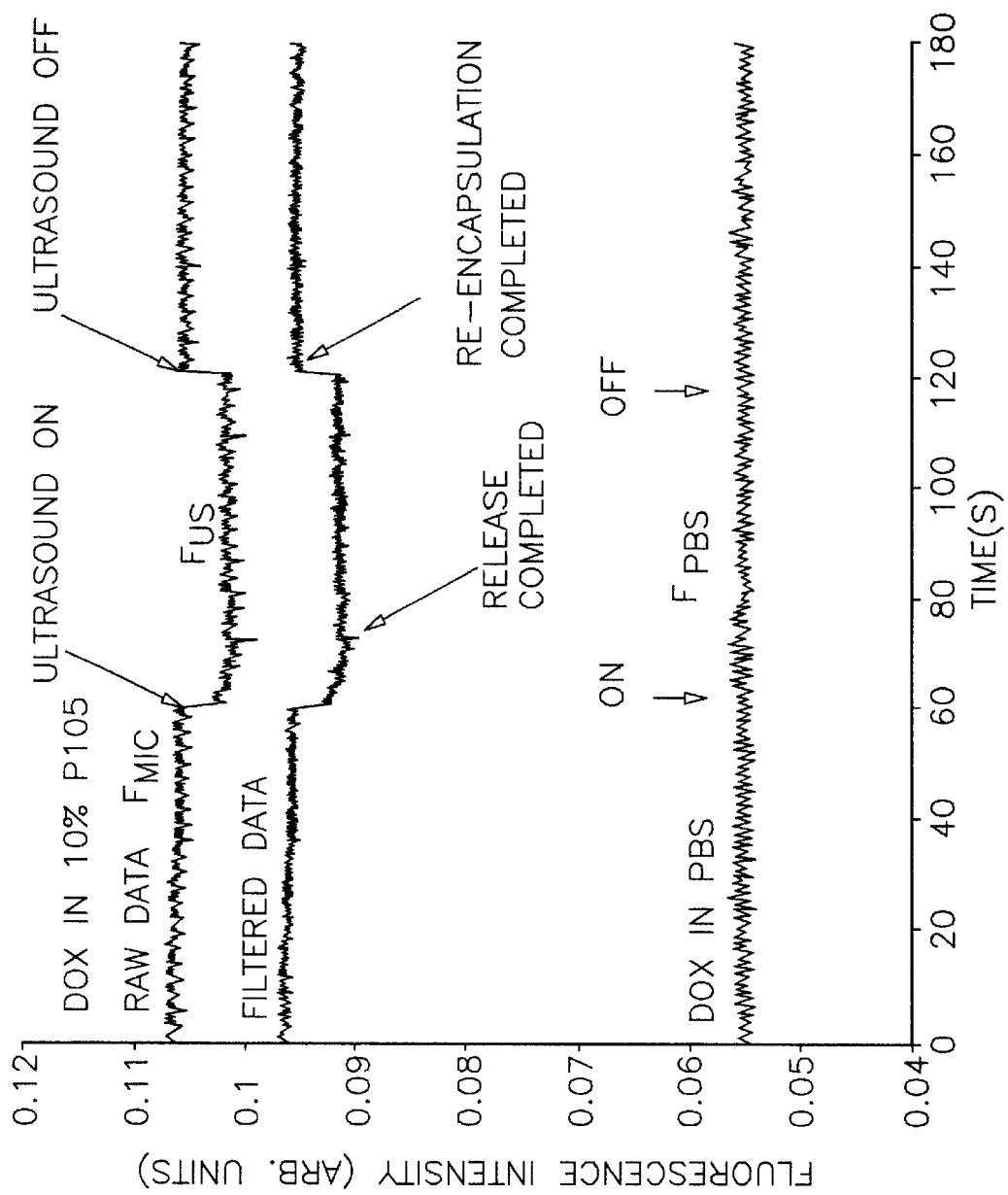
FIG. 19. Example of release profiles of DOX from a 10% P-triblock solution and from PBS. Raw and Fourier-filtered data are presented for the 10% P-triblock solution. For the PBS solution, ultrasound was turned on at 60s and off at 120s; there was a negligible change of DOX fluorescence under sonication.

The experimental procedure is described below. First, fluorescence intensity of drug in phosphate buffered saline, PBS ($F_{PBS}$) was measured; then, without any changes in the experimental setup, the PBS solution was carefully removed and replaced with the drug solution in P-triblock micelles. In all experiments, Rb concentration was 20 μg/ml and DOX concentration was 40 μg/ml. The base fluorescence of the micellar solution ($F_{mic}$) was measured, after which CW or pulsed ultrasound was turned on. During the "ultrasound on" phase, fluorescence dropped as shown in FIG. 19 due to drug release from the hydrophobic core of micelles into the aqueous environment.

Digitized data were analyzed, to calculate the percentage of drug release from micelles. To reduce the noise, the data were Fourier transformed, and a small magnitude narrow band noise of unknown origin and its next three harmonics were filtered out. After Fourier filtering, the data were smoothed using a 10 point moving average. An example of the raw and filtered data is presented in FIG. 19 for DOX release from 10% P-triblock micelles.

The percent of drug release was calculated assuming that $F_{mic}-F_{PBS}$ corresponds to 100% drug release:

$$\text{Release (\%)} = [(F_{mic} - F_{us})/(F_{mic} - F_{PBS})] \times 100\% \tag{1}$$

where $F_{us}$ is fluorescence during exposure to ultrasound.

The data also showed the time required to release the drug from micelles and the time required for drug re-encapsulation once the ultrasound was turned off.

Drugs

Rb was kindly provided by Dr. Shapiro (Institute of Biochemical Physics, Moscow, Russia). DOX was supplied by the University Hospital, University of Utah, Salt Lake City, Utah, USA

Drug Encapsulation in P-triblock Micelles

An aliquot of Rb stock solution in 1:1 $C_2H_5OH$/acetone mixture was evaporated in a vacuum evaporator; PBS or P-triblock solution in PBS was added to the solid Rb residue to produce a final Rb concentration of 20 μg/ml. The system was vortexed for 30 s and then sonicated in a sonication bath operating at 90 kHz until Rb was completely dissolved, which usually took about 15 s.

DOX was introduced into PBS or P-triblock micellar solutions from a stock solution in PBS at a final concentration of 40 μg/ml, followed by a short (15 s) sonication in a sonication bath operating at 90 kHz to facilitate drug encapsulation.

Insonation

Drug release as a function of ultrasound frequency was explored in a low-frequency range, from 20 to 90 kHz; both CW and pulsed ultrasound was investigated. The ultrasound power density was varied from 0 to 3 W/cm$^2$ as measured by a hydrophone as described earlier [34].

The 20-kHz ultrasound was generated by a probe transducer (Sonics and Materials, Newton, Conn.) inserted into the water bath; sonication at 47 kHz was performed in a Cole-Parmer sonication bath (Cole-Parmer Inc., Mount Vernon, Ill.); sonication at 67 and 90 kHz was performed in two different Sonicor SC 100 sonication baths (Sonicor Instruments, Copaique, N.Y.). The power density was controlled by adjusting the a.c. input voltage with a Variac. The 20-kHz ultrasound probe was programmed to generate continuous wave (CW) or pulsed ultrasound of varying power densities and duty cycles; in the pulsed experiments both "ultrasound on" and "ultrasound off" durations were varied. For the sonication baths, pulses were generated by turning the instruments on and off manually.

Ultrasound-induced Radical Formation

Radicals produced upon collapse of transient cavitations were trapped with 5,5-dimethyl-1-pyrroline-N-oxide (DMPO), a radical trap that forms relatively stable adducts with hydroxyl radicals [81]. DMPO was dissolved in PBS at a concentration of 0.1 M. The insonation was performed in darkness; upon the termination of insonation, an aliquot of solution was immediately frozen and kept in liquid nitrogen until the EPR recording.

Results and Discussion

Drug Release Under the Continuous Wave and Pulsed Ultrasound

Using the ultrasonic exposure chamber with real-time fluorescence detection, drug release was measured from micelles under CW or pulsed ultrasound in the frequency range of 20 kHz to 90 kHz.

Figure 20:
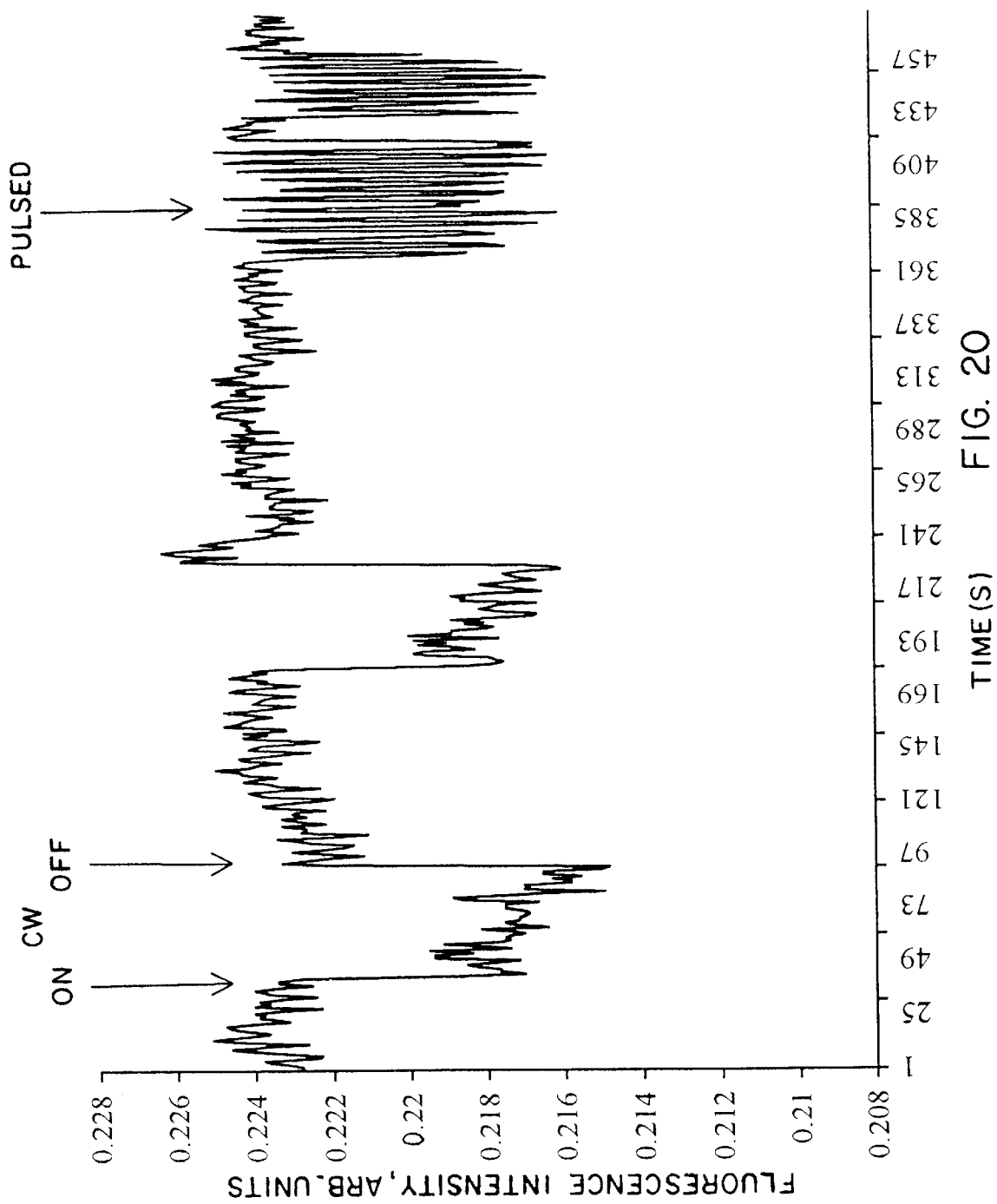
FIG. 20. Rb release profile from 10% P-triblock P-105 micelles at CW and pulsed sonication; Rb concentration 20 μg/ml; ultrasound frequency 47 kHz, power. density 3.5 $W/cm^2$.
Figure 21:
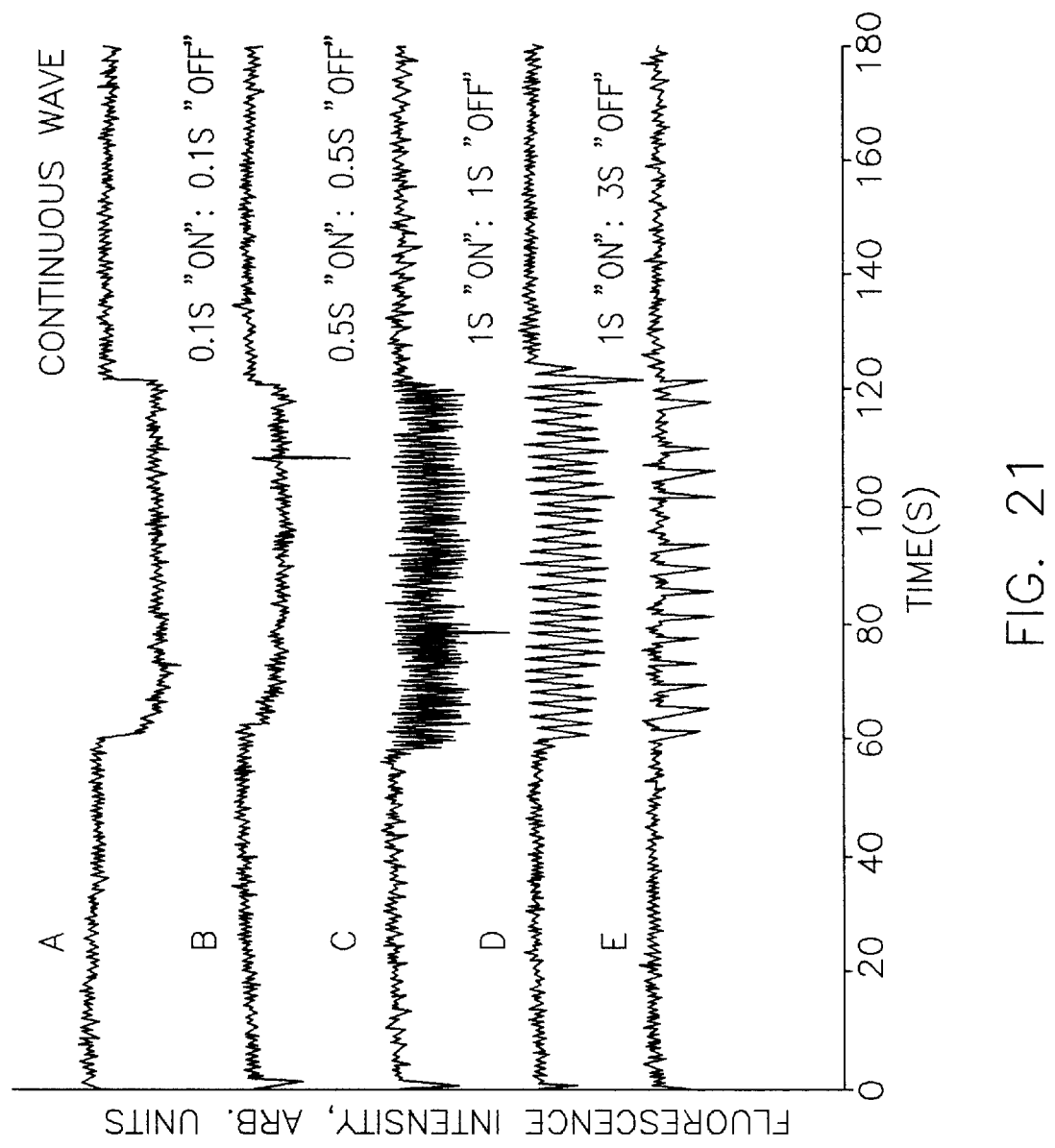
FIG. 21. DOX release profiles from 10% P-triblock P-105 micelles at CW (a) and pulsed (b–e) sonication; DOX concentration 6.7 μg/ml; ultrasound frequency 20 kHz, power density 0.058 $W/cm^2$; pulse sequence: (b)-0.1 s "on": 0.1 s "off"; (c)-0.5 s:0.5 s; (d)-1 s:1 s; e-1 s:3 s.

Examples of the release profiles of drugs from 10% P-triblock micelles are shown in FIG. 20 for Rb at 47-kHz sonication and in FIG. 21 for DOX at 20-kHz sonication respectively; both CW and pulsed ultrasound with various duty cycles were explored.

The drop in fluorescence intensity during the "ultrasound on" phase indicates drug release from the hydrophobic environment of P-triblock micelle cores into the aqueous environment, which may result either from ultrasound-induced drug diffusion out of micelles or from micelle degradation under sonication, as discussed below.

FIGS. 20 and 21 reveal fast re-encapsulation of the released drug during the "ultrasound off" phase of pulsed ultrasound. This is a satisfying finding because it suggests that upon leaving the sonicated volume, the non-extravasated and non-internalized drug would circulate in the encapsulated form, thus preventing unwanted interactions with normal tissues. This is supported by the negligible adsorption or binding of Rb to blood proteins (albumin, fibrinogen) reported elsewhere [82].

When pulse duration was longer than 0.5 s, only negligible differences were observed between the magnitude of the drug release under pulsed ultrasound and that under CW ultrasound (FIGS. 20 and 21).

Effect of Ultrasound Frequency

Drug release as a function of ultrasound frequency was explored in a 438159.1 09032.040 U-2616 low-frequency range, using the following transducers: 20 kHz; 47 kHz; 67 kHz, and 90 kHz. 20 kHz ultrasound was found to most effective. To get comparable release at higher frequencies, greater power densities had to be used. (See Table 3.). This is in agreement with the observations of the effect of ultrasonic frequency on the transdermal penetration of various drugs studied by Mitragotri et al. [83].

Effect of Power Density

For all frequencies studied, the release of drug increased with increasing power density (Table 4). This was true for both stationary release under CW ultrasound and peak release under pulsed ultrasound (data not shown).

Effect of Drug Lipophilicity

At the same frequencies and power densities, the release of DOX from P-triblock micelles was noticeably higher than that of Rb (Table 4). This may be due to the deeper insersion of Rb into the interior of P-triblock micelles reported earlier [72]. This indicates that drug lipophilicity is an important factor determining the extent of acoustically activated drug release from micelles.

Effect of p-Triblock and Drug Concentration

Figure 22:
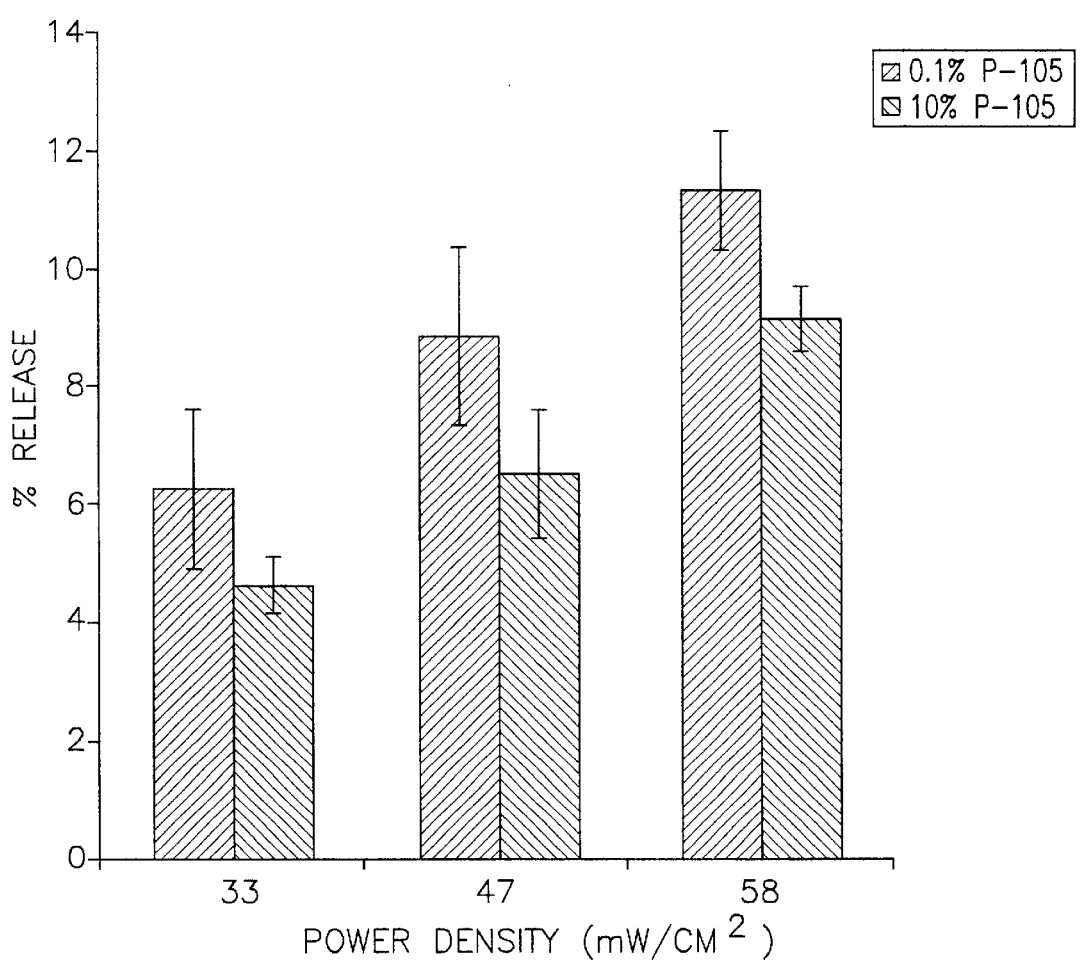
FIG. 22. DOX release from 0. 1% and 10% P-triblock micelles at 20 kHz; DOX concentration 6.7 μg/ml.

Not much difference was observed between Rb (or DOX) release from 10% and 1% P-triblock micelles; however, significantly higher release of Rb and DOX was observed from 0.1% solutions at all frequencies and power densities studied. For Rb, release was between 11 to 13% from 0.1% solution vs. 5.5% from 10% solution (at 67 kHz and 2.8 W/cm$^2$ power density). Data for DOX at 20 kHz are presented in FIG. 22 (note that measurements of drug release from P-triblock solutions of low concentrations are slightly less accurate than those for 10% or 1% solutions because of decreased differences between drug fluorescence in P-triblock and PBS). Higher drug release from P-triblock solutions of lower concentrations may be due to higher local drug concentration in the core of P-triblock micelles when the number of micelles is low, i.e. at P-triblock concentrations only slightly above the corresponding CMC (which is 0.03% for P-105 at 37° C., based on data presented in [84]). This is corroborated by the finding that for the same P-triblock concentration of 10%, drug release indeed increased with increasing initial concentration of drug in the solution. At a concentration of 40 μg/ml, DOX release was 10%±1% (mean and s.d.), while at a concentration of 30 μg/ml, the release was 5.5%±1% (at 67 kHz and 2.8 W/cm² power density). The lower drug release at the lower drug concentration could be attributed to a higher ratio of PPO to DOX in the hydrophobic core of P-triblock micelles, which favors hydrophobic interaction. It is postulated that increased hydrophobic interaction reduces percentage of drug that can be released from micelle core upon the application of ultrasound. This is confirmed by the above mentioned lower release of Rb in comparison to DOX. At higher local drug concentrations in micelle cores, drug/PPO hydrophobic interactions are replaced by weaker drug/drug interactions, which facilitates drug release.

Radical Formation Under Sonication

In parallel with measuring drug release, the threshold for transient cavitation was measured by trapping radicals that were produced upon the collapse of cavitation bubbles. Cavitation threshold increased with increasing ultrasound frequency; at 20 kHz, radicals were observed even at a power density as low as 0.01 W/cm², which is consistent with the relatively high efficiency of 20-kHz ultrasound for drug release from micelles. At 67 kHz, no radicals and no drug release were observed below a power density of 1.0 W/cm². These data are summarized in Table 5.

The data suggest that transient cavitation plays an important role in triggering drug release from micelles. It is hypothesized that shock waves produced by transient cavitation events disrupt micelles and release drug into aqueous environment. During the "ultrasound off" phase, the micelles are restored and drug is re-encapsulated, which takes less than 1 s at 37° C.

The findings described above allow to formulate a new concept of a localized drug delivery, based on drug encapsulating in polymeric micelles to prevent unwanted interactions with normal cells, in combination with focusing ultrasound on the tumor to enhance intracellular drug uptake at the tumor site. Combining micellar drug delivery with acoustic activation of micelles may be developed into a new technique of drug targeting to tumors.

Based on the results presented above, acoustically activated micellar drug delivery is believed to be an effective therapeutic technology for targeted delivery of drugs to solid tumors.

TABLE 3

Effect of ultrasound frequency on DOX release from 10% P-triblock P-105 micelles.

| Frequency | 20 kHz | | | | 67 kHz | | |
|---|---|---|---|---|---|---|---|
| Power Density, W/cm² | 0.033 | 0.047 | 0.058 | 0.15 | 1.35 | 1.66 | 2.8 |
| DOX Release % | 4.6 ± 0.5 | 6.5 ± 1.1 | 9.2 ± 0.56 | 0 | 5.4 ± 2.3 | 8.1 ± 2.1 | 10.7 ± 0.8 |

TABLE 4

Effect of power density on Rb and DOX release from 10% P-triblock P-105 micelles; ultrasound frequency 67 kHz.

| Power Density, W/cm² | Drug Release (%) | |
|---|---|---|
| CW | DOX | Rb |
| 1.35 | 5.4 ± 2.3 | 0.8 ± 0.25 |
| 1.66 | 8.1 ± 2.1 | 3.2 ± 0.9 |
| 2.8 | 10.7 ± 0.8 | 5.5 ± 1.5 |

TABLE 5

Correlation between the formation of transient cavitation and Rb release from P-triblock micelles.

| Ultrasound Frequency, kHz | Power Density, W/cm² | Radical Formation | Drug Release from P-triblock Micelles |
|---|---|---|---|
| 20 | 0.021 | + | Traces |
| | 0.033 | + | + |
| | 0.047 | + | + |
| | 0.058 | + | + |
| 47 | 3.54 | + | + |
| 67 | 0.15 | − | − |
| | 1.0 | traces | − |
| | 1.35 | + | + |
| | 1.66 | + | + |
| | 2.80 | + | + |
| 90 | 0.22 | − | − |
| | 0.83 | − | − |
| | 1.66 | traces | traces |

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:
1. A method for stabilization of a micelle comprising molecules of a block copolymer having a hydrophobic block and a hydrophilic block where the hydrophobic block forms a core of the micelle with corona from the hydrophilic block, the method comprising cross-linking hydrophobic blocks of the molecules without reacting or effecting the function of hydrophilic blocks.

2. The method of claim 1 wherein the cross-linking of the core is initiated by a hydrophobic radical initiator that dissolves only in the hydrophobic blocks of the core.

3. A stabilized micelle comprising molecules of a block polymer having a hydrophobic block and a hydrophilic block where the hydrophobic block forms a core of the micelle with corona from the hydrophilic block, where hydrophobic blocks in the core are cross-linked without reacting or effecting the function of the hydrophilic block.

4. A method for stabilization of a micelle formed from a block polymer having a hydrophobic block and a hydrophilic block where the hydrophobic block forms a core of the micelle with corona from the hydrophilic block, the method comprising introducing an amount of a hydrophobic oil in an amount effective to diffuse into the core and to stabilize the core by increasing the hydrophobicity of the core.

5. The method of claim 4 wherein the oil is a vegetable oil.

6. A stabilized micelle comprising molecules of a block polymer having a hydrophobic block and a hydrophilic block where the hydrophobic block forms a core of the micelle with corona from the hydrophilic block, with a hydrophobic oil in the hydrophobic blocks in an amount sufficient to stabilize the core.

7. A method for stabilization of a micelle formed from a block polymer having a hydrophobic block and a hydrophilic block where the hydrophobic block forms a core of the micelle with corona from the hydrophilic block, the method comprising polymerizing a stimuli-responsive hydrogel in the micelle core to form an interpenetrating network in the core.

8. A method for stabilization of a micelle formed from a block polymer having a hydrophobic block and a hydrophilic block where the hydrophobic block forms a core of the micelle with corona from the hydrophilic block, the method comprising polymerizing a temperature-responsive LCST hydrogel in the micelle core to form an interpenetrating network in the core.

9. The method of claim 7 wherein the hydrogel is pH responsive.

10. A stabilized micelle comprising molecules of a block polymer having a hydrophobic block and a hydrophilic block where the hydrophobic block forms a core of the micelle with corona from the hydrophilic block, the core stabilized with a stimuli-responsive low critical solution temperature (LCST) hydrogel in the micelle core forming an interpenetrating network in the core.

11. A method for stabilization of a micelle formed from a block polymer having a hydrophobic block and a hydrophilic block where the hydrophobic block forms a core of the micelle with corona from the hydrophilic block, the method comprising polymerizing a temperature-responsive low critical solution hydrogel in the micelle core to form an interpenetrating network in the core, using an initiator that is hydrophobic such that polymerization of hydrogel occurs predominantly in the core, with only a minor amount occurring outside of the core.

12. A method for manufacture of a stabilized micelle delivery system for a lipophilic or hydrophilic substance comprising:
stabilizing micelles comprising a block polymer having a hydrophobic block and a hydrophilic block where the hydrophobic block forms a core of the micelle with corona from the hydrophilic block, the method comprising polymerizing a hydrogel with a temperature-responsive low critical solution temperature (LCST) in the micelle core to form an interpenetrating network in the core, using an initiator that is hydrophobic such that polymerization of hydrogel occurs in the core, with only a minor amount occurring outside of the core;
controlling the temperature of the micelles to achieve a first temperature which is below the LCST such that the hydrogel in the core of the micelle is in a swollen state sufficient to swell the core of the micelle;
loading substances into the micelles to diffuse the substance into the swollen cores of the micelles, and
controlling the temperature of the micelles to achieve a second temperature of the micelles above the LCST at which the gel collapses to a dense phase to form dense core in which the substance is retained in the core.

13. The method of claim 12 wherein the substance is a drug.

14. The method of claim 12 wherein the temperature-responsive hydrogel is selected from the group consisting of N-isopropylacrylamide, N,N-diethylacrylamide N,N-diethylmethacrylamide, N-isopropylmethacrylamide, N-n-butylacrylamide, other mono- and di-alkyl substituted acrylamides, acrylic acid, methacrylic acid, and mixtures thereof.

15. The method of claim 12 wherein temperature responsive hydrogel is copolymerized with a monomer to change the LCST.

16. The method of claim 12 wherein temperature responsive hydrogel is copolymerized with acrylic acid to shift the LCST upward.

17. The method of claim 12 wherein temperature responsive hydrogel is copolymerized with, and the use of hydrophobic butyl acrylate to shift the LCST downward.

18. The method of claim 12 wherein temperature responsive hydrogel is copolymerized with acylamide, acrylic, or methacrylic comonomer to change the LCST.

19. The method of claim 12 wherein polymerized hydrogel segments are formed that have a MW less than 20,000 Daltons.

20. The method of claim 12 wherein the block polymer is p-triblock.

21. The method of claim 13 wherein the drug is released from the stabilized micelle by subjecting the micelle to a pulsed ultrasound signal.

22. A method for administering a hydrophobic drug to a patient, the method comprising:
stabilizing micelles comprising a block polymer having a hydrophobic block and a hydrophilic block where the hydrophobic block forms a core of the micelle with corona from the hydrophilic block, the method comprising polymerizing a hydro gel with a temperature-responsive low critical solution temperature (LCST) in the micelle core to form an interpenetrating network in the core, using an initiator that is hydrophobic such that polymerization of hydrogel occurs in the core, with only a minor amount occurring outside of the core,
controlling the temperature of the micelles to achieve a first temperature which is below the LCST such that the hydrogel in the core of the micelle is in a swollen state sufficient to swell the core of the micelle,
loading the drugs into the micelles to diffuse drug into the swollen cores of the micelles,
controlling the temperature of the micelles to achieve a second temperature near the temperature of the body, which temperature is above the LCST at which the gel collapses to a dense phase to form dense core in which drug is retained in the core,
administering the micelles into the patient's bloodstream or desired site in the patient's body, and subjecting a region of the body to which the drug is to be administered to pulsed ultrasound signal in which pulses are timed to release the drug when the ultrasound is on.

23. The method of claim 11 wherein the temperature-responsive hydrogel is selected from the group consisting of N-isopropylacrylamide, N,N-diethylacrylamide N,N-diethylmethacrylamide, N-isopropylmethacrylamide, N-n-butylacrylamide, other mono- and di-alkyl substituted acrylamides, acrylic acid, methacrylic acid, and mixtures thereof.

24. The method of claim 11 wherein temperature responsive hydrogel is copolymerized with a monomer to change the LCST.

25. The method of claim 11 wherein temperature responsive hydrogel is copolymerized with acrylic acid to shift the LCST upward.

26. The method of claim 11 wherein temperature responsive hydrogel is copolymerized with, and the use of hydrophobic butyl acrylate to shift the LCST downward.

27. The method of claim 11 wherein temperature responsive hydrogel is copolymerized with acylamide, acrylic, or methacrylic comonomer to change the LCST.

28. The method of claim 11 wherein polymerized hydrogel segments are formed that have a MW less than 20,000 Daltons.

29. The method of claim 11 wherein the block polymer is p-triblock.

30. The method of claim 11 wherein the drug is released from the stabilized micelle by subjecting the micelle to a pulsed ultrasound signal.

31. A method for manufacturing a stabilized micelle delivery system for a lipophilic or hydrophilic substance, the method comprising:

stabilizing micelles comprising a block polymer having a hydrophobic block and a hydrophilic block where the hydrophobic block forms a core of the micelle with a corona from the hydrophilic block, said stabilizing comprising polymerizing a hydrogel with a temperature-responsive low critical solution temperature (LCST) in the micelle core to form an interpenetrating network in the core, using an initiator that is hydrophobic such that polymerization of the hydrogel occurs in the core, with only a minor amount occurring outside of the core, wherein the hydrogel is selected from the group consisting of N-isopropylacrylamide, N,N-diethylacrylamide N,N-diethylmethacrylamide, N-isopropylmethacrylamide, N-n-butylacrylamide, other mono- and di-alkyl substituted acrylamides, acrylic acid, methacrylic acid, and mixtures thereof;

controlling the temperature of the micelles to achieve a first temperature which is below the LCST such that the hydrogel in the core of the micelle is in a swollen state sufficient to swell the core of the micelle;

loading substances into the micelles to diffuse the substance into the swollen cores of the micelles, and controlling the temperature of the micelles to achieve a second temperature of the micelles above the LCST at which the gel collapses to a dense phase to form dense core in which the substance is retained in the core.

32. A method for manufacturing a stabilized micelle delivery system for a lipophilic or hydrophilic substance, the method comprising:

stabilizing micelles comprising a block polymer having a hydrophobic block and a hydrophilic block where the hydrophobic block forms a core of the micelle with a corona from the hydrophilic block, said stabilizing comprising polymerizing a hydrogel with a temperature-responsive low critical solution temperature (LCST) in the micelle core to form an interpenetrating network in the core, using an initiator that is hydrophobic such that polymerization of the hydrogel occurs in the core, with only a minor amount occurring outside of the core, wherein the hydrogel is copolymerized with acrylic acid to shift the LCST upward;

controlling the temperature of the micelles to achieve a first temperature which is below the LCST such that the hydrogel in the core of the micelle is in a swollen state sufficient to swell the core of the micelle;

loading substances into the micelles to diffuse the substance into the swollen cores of the micelles, and controlling the temperature of the micelles to achieve a second temperature of the micelles above the LCST at which the gel collapses to a dense phase to form dense core in which the substance is retained in the core.

33. A method for manufacturing a stabilized micelle delivery system for a lipophilic or hydrophilic substance, the method comprising:

stabilizing micelles comprising a block polymer having a hydrophobic block and a hydrophilic block where the hydrophobic block forms a core of the micelle with a corona from the hydrophilic block, said stabilizing comprising polymerizing a hydrogel with a temperature-responsive low critical solution temperature (LCST) in the micelle core to form an interpenetrating network in the core, using an initiator that is hydrophobic such that polymerization of the hydrogel occurs in the core, with only a minor amount occurring outside of the core, wherein the hydrogel is copolymerized with hydrophobic butyl acrylate to shift the LCST downward;

controlling the temperature of the micelles to achieve a first temperature which is below the LCST such that the hydrogel in the core of the micelle is in a swollen state sufficient to swell the core of the micelle;

loading substances into the micelles to diffuse the substance into the swollen cores of the micelles, and controlling the temperature of the micelles to achieve a second temperature of the micelles above the LCST at which the gel collapses to a dense phase to form dense core in which the substance is retained in the core.

34. A method for manufacturing a stabilized micelle delivery system for a lipophilic or hydrophilic substance, the method comprising:

stabilizing micelles comprising a block polymer having a hydrophobic block and a hydrophilic block where the hydrophobic block forms a core of the micelle with a corona from the hydrophilic block, said stabilizing comprising polymerizing a hydrogel with a temperature-responsive low critical solution temperature (LCST) in the micelle core to form an interpenetrating network in the core, using an initiator that is hydrophobic such that polymerization of the hydrogel occurs in the core, with only a minor amount occurring outside of the core, wherein the hydrogel is copolymerized with acylamide, acrylic, or methacrylic comonomer to change the LCST;

controlling the temperature of the micelles to achieve a first temperature which is below the LCST such that the hydrogel in the core of the micelle is in a swollen state sufficient to swell the core of the micelle;

loading substances into the micelles to diffuse the substance into the swollen cores of the micelles, and controlling the temperature of the micelles to achieve a second temperature of the micelles above the LCST at which the gel collapses to a dense phase to form dense core in which the substance is retained in the core.

35. A method for manufacturing a stabilized micelle delivery system for a drug, wherein the drug is released from the stabilized micelle by subjecting the stabilized micelle to a pulsed ultrasound signal, the method comprising:

stabilizing micelles comprising a block polymer having a hydrophobic block and a hydrophilic block where the hydrophobic block forms a core of the micelle with a corona from the hydrophilic block, said stabilizing comprising polymerizing a hydrogel with a temperature-responsive low critical solution temperature (LCST) in the micelle core to form an interpenetrating network in the core, using an initiator that is hydrophobic such that polymerization of the hydrogel occurs in the core, with only a minor amount occurring outside of the core;

controlling the temperature of the micelles to achieve a first temperature which is below the LCST such that the hydrogel in the core of the micelle is in a swollen state sufficient to swell the core of the micelle;

loading the drug into the micelles to diffuse the drug into the swollen cores of the micelles; and controlling the temperature of the micelles to achieve a second temperature of the micelles above the LCST at which the gel collapses to a dense phase to form dense core in which the drug is retained in the core.

36. A method for stabilizing a micelle formed from a block polymer having a hydrophobic block and a hydrophilic block where the hydrophobic block forms a core of the micelle with a corona from the hydrophilic block, the method comprising polymerizing a temperature-responsive low critical solution temperature (LCST) hydrogel in the micelle core to form an interpenetrating network in the core, using an initiator that is hydrophobic such that polymerization of hydrogel occurs predominantly in the core, with only a minor amount occurring outside of the core, wherein the hydrogel is selected from the group consisting of N-isopropylacrylamide, N,N-diethylacrylamide N,N-diethylmethacrylamide, N-isopropylmethacrylamide, N-n-butylacrylamide, other mono- and di-alkyl substituted acrylamides, acrylic acid, methacrylic acid, and mixtures thereof.

37. A method for stabilizing a micelle formed from a block polymer having a hydrophobic block and a hydrophilic block where the hydrophobic block forms a core of the micelle with a corona from the hydrophilic block, the method comprising polymerizing a temperature-responsive low critical solution temperature (LCST) hydrogel in the micelle core to form an interpenetrating network in the core, using an initiator that is hydrophobic such that polymerization of hydrogel occurs predominantly in the core, with only a minor amount occurring outside of the core, wherein the hydrogel is copolymerized with hydrophobic butyl acrylate to shift the LCST downward.

38. A method for stabilizing a micelle formed from a block polymer having a hydrophobic block and a hydrophilic block where the hydrophobic block forms a core of the micelle with a corona from the hydrophilic block, the method comprising polymerizing a temperature-responsive low critical solution temperature (LCST) hydrogel in the micelle core to form an interpenetrating network in the core, using an initiator that is hydrophobic such that polymerization of hydrogel occurs predominantly in the core, with only a minor amount occurring outside of the core, wherein the hydrogel is copolymerized with acylamide, acrylic, or methacrylic comonomer to change the LCST.

39. A method for stabilizing a micelle formed from a block polymer having a hydrophobic block and a hydrophilic block where the hydrophobic block forms a core of the micelle with a corona from the hydrophilic block, wherein the stabilized micelle releases a substance contained therein in response to a pulsed ultrasound signal, the method comprising polymerizing a temperature-responsive low critical solution temperature (LCST) hydrogel in the micelle core to form an interpenetrating network in the core, using an initiator that is hydrophobic such that polymerization of hydrogel occurs predominantly in the core, with only a minor amount occurring outside of the core.

* * * * *